(12) United States Patent
Howard et al.

(10) Patent No.: US 11,583,312 B2
(45) Date of Patent: Feb. 21, 2023

(54) TRANSSEPTAL CROSSING SYSTEM

(71) Applicant: Cross Vascular, Inc., Solana Beach, CA (US)

(72) Inventors: Steven Howard, La Jolla, CA (US); Marshall L. Sherman, Cardiff By The Sea, CA (US); Randell Werneth, Rancho Santa Fe, CA (US); Bradley Klos, Solana Beach, CA (US)

(73) Assignee: Cross Vascular, Inc., Solana Beach, CA (US)

( * ) Notice: Subject to any disclaimer, the term of this patent is extended or adjusted under 35 U.S.C. 154(b) by 0 days.

(21) Appl. No.: 17/411,555

(22) Filed: Aug. 25, 2021

(65) Prior Publication Data

US 2022/0061909 A1 Mar. 3, 2022

Related U.S. Application Data

(60) Provisional application No. 63/195,578, filed on Jun. 1, 2021, provisional application No. 63/070,167, filed on Aug. 25, 2020.

(51) Int. Cl.
*A61B 18/14* (2006.01)
*A61B 17/34* (2006.01)
(Continued)

(52) U.S. Cl.
CPC ...... *A61B 17/3421* (2013.01); *A61B 18/1206* (2013.01); *A61B 18/14* (2013.01);
(Continued)

(58) Field of Classification Search
CPC . A61B 18/1477; A61B 18/1206; A61B 18/14; A61B 18/1402; A61B 2018/1425;
(Continued)

(56) References Cited

U.S. PATENT DOCUMENTS

| 5,190,528 A | 3/1993 | Fonger et al. |
| 6,231,546 B1 | 5/2001 | Milo et al. |

(Continued)

FOREIGN PATENT DOCUMENTS

| CN | 2291901 | 9/1998 |
| CN | 105193476 A | 12/2015 |

(Continued)

OTHER PUBLICATIONS

Clinical Analysis of RF Transseptal Puncture, NRG Transseptal Needle, USA, Canada, Baylis Medical Company, Inc., 2016.

(Continued)

*Primary Examiner* — Michael F Peffley
(74) *Attorney, Agent, or Firm* — Knobbe, Martens, Olson & Bear, LLP

(57) ABSTRACT

A self-contained, battery powered transseptal crossing system is disclosed. An elongate, flexible electrically conductive needle body has a proximal end and a distal end. An insulation layer surrounds the sidewall and leaves exposed a distal electrode tip. A generator is configured to deliver RF energy to the electrode tip, and includes a processor configured to take impedance measurements at the tip to confirm contact with the intra atrial septum and/or confirm entry into the left atrium.

20 Claims, 19 Drawing Sheets

(51) Int. Cl.
*A61B 18/12* (2006.01)
*A61B 17/00* (2006.01)
*A61B 18/00* (2006.01)

(52) U.S. Cl.
CPC *A61B 18/1477* (2013.01); *A61B 2017/00026* (2013.01); *A61B 2017/00128* (2013.01); *A61B 2017/00199* (2013.01); *A61B 2017/00247* (2013.01); *A61B 2017/3433* (2013.01); *A61B 2018/0016* (2013.01); *A61B 2018/00077* (2013.01); *A61B 2018/00083* (2013.01); *A61B 2018/00357* (2013.01); *A61B 2018/00577* (2013.01); *A61B 2018/00875* (2013.01); *A61B 2018/1226* (2013.01); *A61B 2018/1425* (2013.01)

(58) Field of Classification Search
CPC .... A61B 2018/143; A61B 2018/00452; A61B 2018/1475; A61B 2018/00577; A61B 2018/00767; A61B 2018/1226; A61B 2018/1366; A61B 2018/00589; A61B 2018/00636; A61B 2018/00875
See application file for complete search history.

(56) References Cited

U.S. PATENT DOCUMENTS

| | | | |
|---|---|---|---|
| 6,565,562 | B1 * | 5/2003 | Shah .......... A61B 18/1492 128/898 |
| 6,650,923 | B1 | 11/2003 | Lesh et al. |
| 7,048,733 | B2 | 5/2006 | Hartley et al. |
| 7,112,197 | B2 | 9/2006 | Hartley et al. |
| 7,270,662 | B2 | 9/2007 | Visram et al. |
| 7,947,040 | B2 | 5/2011 | Davies et al. |
| 8,092,450 | B2 | 1/2012 | Davies et al. |
| 8,192,425 | B2 | 6/2012 | Mirza et al. |
| 8,457,714 | B2 | 6/2013 | Shachar et al. |
| 8,500,768 | B2 | 8/2013 | Cohen |
| 8,679,107 | B2 | 3/2014 | Mirza et al. |
| 8,834,384 | B2 | 9/2014 | Krishnan |
| 8,992,556 | B2 | 3/2015 | Chanduszko et al. |
| 9,095,350 | B2 | 8/2015 | Condie et al. |
| 9,179,932 | B2 | 11/2015 | Davies et al. |
| 9,415,188 | B2 | 8/2016 | He et al. |
| 9,504,398 | B2 | 11/2016 | Krishnan |
| 9,510,900 | B2 | 12/2016 | Abou-Marie et al. |
| 9,585,692 | B2 | 3/2017 | Kurth et al. |
| 9,597,146 | B2 | 3/2017 | Davies et al. |
| 10,166,070 | B2 | 1/2019 | Davies et al. |
| 10,172,632 | B2 | 1/2019 | Morero et al. |
| 10,183,151 | B2 | 1/2019 | Alvarez et al. |
| 10,485,569 | B2 | 11/2019 | Lenker et al. |
| 10,493,259 | B2 | 12/2019 | Urbanski et al. |
| 10,610,297 | B2 | 4/2020 | Leung et al. |
| 10,639,060 | B2 | 5/2020 | Vardi et al. |
| 10,716,920 | B2 | 7/2020 | Kurth et al. |
| 10,820,925 | B2 | 11/2020 | Urbanski et al. |
| 10,856,902 | B2 | 12/2020 | Leeflang et al. |
| 11,007,016 | B2 | 5/2021 | Kusumoto |
| 11,172,984 | B2 | 11/2021 | Sharma et al. |
| 2002/0095152 | A1 | 7/2002 | Ciarrocca et al. |
| 2003/0163153 | A1 | 8/2003 | Scheib |
| 2004/0133113 | A1 * | 7/2004 | Krishnan .......... A61M 25/0662 600/508 |
| 2004/0143261 | A1 | 7/2004 | Hartley et al. |
| 2004/0220461 | A1 | 11/2004 | Schwartz |
| 2005/0149097 | A1 | 7/2005 | Regnell et al. |
| 2006/0241583 | A1 * | 10/2006 | Malecki .......... A61B 18/1492 606/41 |
| 2008/0140073 | A1 | 6/2008 | Schwartz |
| 2008/0208184 | A1 | 8/2008 | Davies |
| 2009/0012517 | A1 * | 1/2009 | de la Rama .......... A61B 34/73 606/41 |
| 2010/0191142 | A1 * | 7/2010 | Paul .......... A61B 5/015 600/549 |
| 2011/0224666 | A1 | 9/2011 | Davies et al. |
| 2012/0232546 | A1 | 9/2012 | Mirza et al. |
| 2014/0100561 | A1 * | 4/2014 | Biadillah .......... A61B 18/18 606/33 |
| 2014/0107644 | A1 | 4/2014 | Falwell et al. |
| 2014/0206987 | A1 * | 7/2014 | Urbanski .......... A61M 5/007 600/424 |
| 2015/0157353 | A1 | 6/2015 | Lenker et al. |
| 2015/0182255 | A1 | 7/2015 | Shivkumar |
| 2015/0265344 | A1 | 9/2015 | Aktas et al. |
| 2016/0262795 | A1 | 9/2016 | Urbanski et al. |
| 2017/0135559 | A1 | 5/2017 | Horrisberger et al. |
| 2017/0360498 | A1 | 12/2017 | Davies et al. |
| 2018/0028258 | A1 | 2/2018 | Zamarripa et al. |
| 2018/0064915 | A1 | 3/2018 | Kurth et al. |
| 2018/0070982 | A1 | 3/2018 | Kimmel et al. |
| 2018/0289388 | A1 * | 10/2018 | Lenker .......... A61B 18/1492 |
| 2019/0274581 | A1 | 9/2019 | Mosesov et al. |
| 2019/0374281 | A1 | 12/2019 | Davies et al. |
| 2020/0060710 | A1 * | 2/2020 | Urbanski .......... A61B 17/3205 |
| 2020/0196908 | A1 | 6/2020 | Ben-haim et al. |
| 2021/0068892 | A1 * | 3/2021 | Urbanski .......... A61B 5/4836 |
| 2021/0121227 | A1 | 4/2021 | Davies et al. |
| 2021/0401483 | A1 | 12/2021 | Highsmith et al. |
| 2022/0061884 | A1 | 3/2022 | Howard et al. |
| 2022/0061911 | A1 | 3/2022 | Howard et al. |
| 2022/0110577 | A1 | 4/2022 | Highsmith et al. |
| 2022/0354533 | A1 | 11/2022 | Lenker |

FOREIGN PATENT DOCUMENTS

| | | |
|---|---|---|
| WO | WO 2002/058780 | 8/2002 |
| WO | WO 2005/046487 | 5/2005 |
| WO | WO 2008/008796 | 1/2008 |
| WO | WO 2013/101632 | 7/2013 |
| WO | WO 2014/089373 | 6/2014 |
| WO | WO 2018/165277 | 9/2018 |
| WO | WO 2021/014316 | 1/2021 |
| WO | WO 2022/046777 | 3/2022 |

OTHER PUBLICATIONS

International Search Report and Written Opinion, Application No. PCT/US2021/031827, dated Oct. 20, 2021.
International Search Report and Written Opinion in corresponding International Patent Application No. PCT/US2021/047361, dated Jan. 27, 2022, in 10 pages.

* cited by examiner

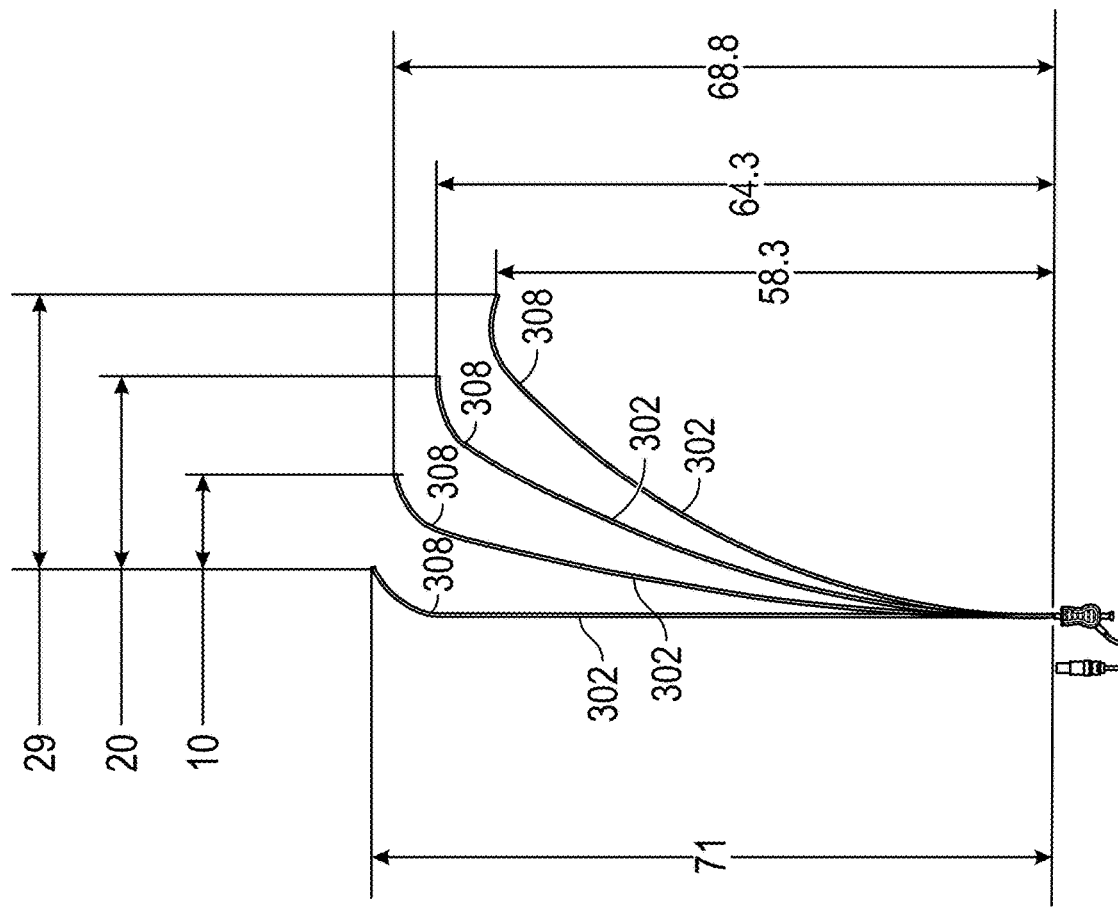

TRANSSEPTAL CROSSING SYSTEM

CROSS-REFERENCE TO RELATED APPLICATIONS

This application claims the priority benefit under 35 U.S.C. § 119(e) of U.S. Provisional Application No. 63/070,167, filed Aug. 25, 2020 and U.S. Provisional Application No. 63/195,578, filed Jun. 1, 2021, the entireties of which are hereby incorporated by reference herein.

BACKGROUND OF THE INVENTION

Transseptal crossing is used to access the left atrium crossing from the right atrium through the septal wall for any of a variety of electrophysiology (EP) or structural heart procedures. For example, the left atrium may be accessed to assess hemodynamics and/or perform a mitral valve repair or replacement procedure or mitral valvuloplasty, to accommodate transvascular atrial fibrillation (AF) ablation procedures, or to implant left atrial occlusion devices among other procedures.

Crossing the septum normally requires locating and puncturing the fossa ovalis to access the left atrium. Locating the fossa ovalis may be accomplished using fluoroscopy and ultrasound, and potentially echocardiography.

Mechanical puncture through the tissue of the fossa ovalis can be accomplished using a piercing tool such as a standard Brockenbrough needle as is understood in the art. Alternatively, a transseptal needle having a radio frequency energized tip and pressure sensing or contrast injection to confirm penetration may be used, such as those produced by Baylis Medical Company, Inc.

Notwithstanding the foregoing, there remains a need for an improved transseptal crossing needle and associated sheath and dilator system.

SUMMARY OF THE INVENTION

There is provided in accordance with one aspect of the present invention, a transseptal crossing system. The system includes a transseptal crossing needle comprising an elongate, flexible tubular body, having a proximal end, a distal end and an electrically conductive sidewall defining a central lumen. An insulation layer surrounds the sidewall, leaving exposed a distal electrode tip. An end aperture extends distally from the central lumen through the distal electrode tip. A battery powered RF generator is configured to deliver RF energy to the electrode tip and also to measure impedance at the tip to provide information about the location of the electrode tip.

At least one side port may be provided through the tubular body, spaced proximally of the electrode tip. The needle may further comprise at least one side electrode on the tubular body spaced proximally of the electrode tip. The side electrode may be in the form of an annular ring.

The tubular body may have a step down in outside diameter, and may have a maximum outside diameter of about 0.035 inches. The distal electrode may comprise a smooth, hemispherical surface. The sidewall may comprise a stainless steel tube.

The tubular body may have sufficient structural integrity to guide a large bore catheter transvascularly through a septal wall and into a left atrium of the heart, and may have sufficient structural integrity to guide a large bore catheter transvascularly through a septal wall and into a left atrial appendage of the heart There is also provided a method of providing access to the left atrium, comprising the steps of transvascularly advancing a transseptal needle into the right atrium and into contact with the fossa; taking a first impedance measurement at the fossa; transmitting RF energy from a battery powered generator through the needle and to the fossa to penetrate the fossa and enter the left atrium; and taking a second impedance measurement to confirm location of the needle in the left atrium.

The transvascularly advancing step may comprise advancing an assembly of the needle, a dilator and a sheath. The method may further comprise the step of taking at least a third impedance measurement with an electrode on the sheath.

There is provided in accordance with another aspect of the present invention a depth sensing dilator system for dilating a penetration in a tissue plane. The system comprises an elongate flexible body, having a proximal end and a distal end; a tapered dilator segment on the body; at least a first and second electrode spaced axially apart on the body; a processor; and an output.

The processor may be configured to send a first signal to the output when the first electrode reaches a predetermined relationship with the tissue plane, and to send a second signal to the output when the second electrode reaches the predetermined relationship with the tissue plane.

The predetermined relationship may be when the electrode first contacts the tissue plane, or when the electrode passes through the tissue plane such as into a blood pool beyond the tissue plane. The output may comprise at least one of an audio output, a visual output, or a tactile output.

The at least one electrode may be on the tapered dilator segment. The first and second electrodes may be spaced axially apart on the tapered dilator segment. The dilator system may further comprise a third electrode on the distal end. The first, second and third electrodes may be approximately equally axially spaced apart.

The depth sensing dilator system may further comprise an RF generator configured to deliver RF energy to at least one of the first and second electrodes. The system may be configured to determine impedance at at least one of the electrodes. The RF generator may be battery powered.

There is also provided a method of sensing the depth of penetration of an intravascular device through a tissue plane. The method comprises the steps of providing an intravascular device having an elongate flexible body, having a proximal end and a distal end and at least a first and second electrode spaced axially apart on the body; advancing the body through the tissue plane; generating a first output when the first electrode first contacts or penetrates through the tissue plane; and generating a second output when the second electrode first contacts or penetrates through the tissue plane.

The tissue plane may be the atrial septum. The intravascular device may be a dilator, having a tapered distal dilator segment. The dilator may comprises at least three electrodes spaced axially apart along the dilator segment.

There is provided in accordance with another aspect of the present invention a transseptal crossing needle. The needle comprises an elongate, flexible tubular body, having a proximal end, a distal end and an electrically conductive sidewall defining a central lumen. A radially inwardly extending annular recess is provided at the distal end of the tubular body. The tubular body may have a first outside diameter proximally of the annular recess and the annular recess may have a second, smaller outside diameter.

An electrode tip may have a proximally extending annular flange residing within the annular recess on the tubular body, and the electrode tip may have a third outside diameter distally of the annular flange and greater than the first diameter. An insulation layer may surround the sidewall and the annular flange, the insulation layer having an outside diameter across the junction of the annular flange and tubular body of approximately the same as the third diameter.

The needle may additionally comprise an end aperture extending distally from the central lumen through the distal electrode tip. The needle may further comprise at least one side port through the tubular body spaced proximally of the electrode tip.

The transseptal crossing needle may further comprise at least one side electrode on the tubular body spaced proximally of the electrode tip; the tubular body may comprise a step down in outside diameter; and the distal electrode tip may comprise a smooth, hemispherical electrode surface.

The electrode tip may comprise a different material than the tubular body. The electrode tip may comprises gold, and the tubular body may comprise stainless steel. The outside diameter of the annular flange may be spaced radially inwardly from the maximum outside diameter of the electrode tip by at least about 0.002 inches. The wall thickness of the annular flange may be within the range of from about 0.002 inches to about 0.005 inches.

Further features and advantages of the present invention will become apparent to those of skill in the art in view of the detailed description which follows, considered along with the associated drawings and claims.

BRIEF DESCRIPTION OF THE DRAWINGS

FIGS. 16A-16D show RF needles with pre-set curves.

DETAILED DESCRIPTION OF THE PREFERRED EMBODIMENT

Figure 1A:
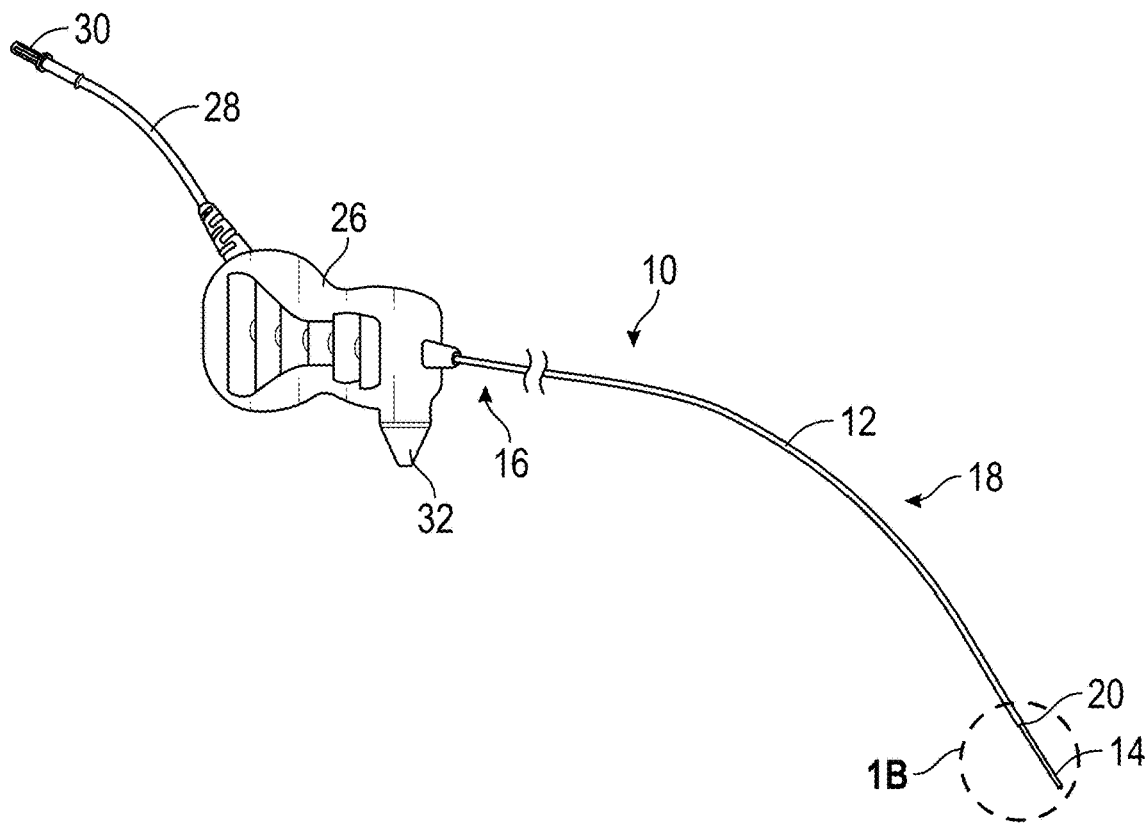
FIG. 1A schematically illustrates a transseptal crossing needle in accordance with the present invention.
Figure 1B:
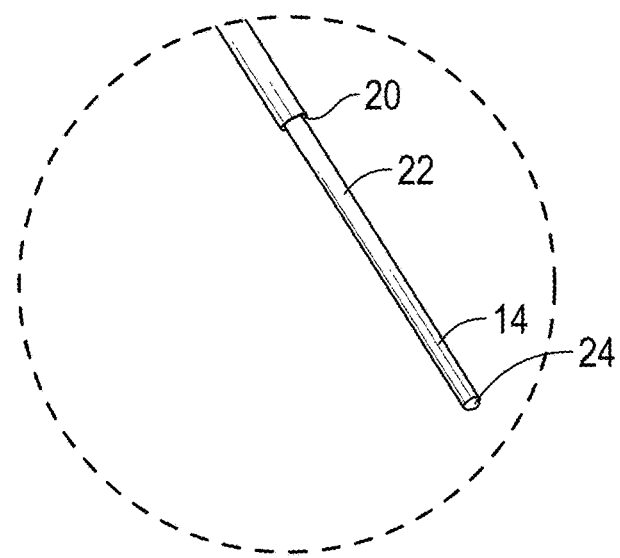
FIG. 1B is a detail perspective view of a distal end of the needle of FIG. 1A.

FIGS. 1A and 1B illustrate an embodiment of a tissue penetrating apparatus 10 in a transseptal crossing system. Apparatus 10 comprises an elongate, flexible needle body 12 having a distal end 14 and a proximal end 16. The needle body 12 is configured to be inserted within and advanced along a lumen of a body of a patient, such as a patient's vasculature, and maneuverable therethrough to a desired location proximate material, such as tissue, to be perforated. In one implementation, the needle body 12 is configured for femoral vein access and transvascular navigation into the right atrium, across the fossa ovalis and into the left atrium.

A distal zone 18 may be provided with a preset curve during manufacturing, typically by mechanically bending in the case of a metal tubular body, or exposing it to heat while it is fixed in a desired shape for a polymeric extrusion. In an alternate embodiment, the shape of distal region is additionally or alternatively modifiable by the operator during use.

The distal zone 18 may include a transition 20 between a larger diameter proximal portion of needle body 12 and a smaller outer diameter advance segment 22 that extends between the transition 20 and the distal end 14. The transition 20 may provide tactical feedback once the advance segment 22 has advanced through the perforation. In some embodiments, the outer diameter of distal advance segment 22 may be no larger than about 0.8 mm to about 1.0 mm. For example, the outer diameter of advance segment 22 may be about 0.9 mm (about 0.035"). The outer diameter of needle body 12 proximal to the transition 20 may be no larger than about 0.040" to about 0.060". For example, the outer diameter of needle body 12 may be about 0.050" (1.282 mm).

The distal end 14 terminates in a conductive electrode tip 24, variations of which are discussed below. The electrode tip 24 enables delivery of RF energy for piercing tissue, and optionally enables use as an ECG measuring device and/or an impedance measuring device. The electrode tip 24 and optionally the entire needle body 12 and advance segment 22 may comprise a conductive and optionally radiopaque material, such as stainless steel, tungsten, platinum, or another electrically conductive metal. If the needle body is not radiopaque, one or more radiopaque markers may be affixed to needle body 12 such as to highlight the location of the transition 20 or other important landmarks on apparatus 10.

The needle body 12 may comprise a hypotube, having a central lumen extending axially throughout its length. The advance segment 22 may be a smaller diameter hypotube, and may be provided with one or two or three or more ports such as an end port through the electrode tip 24 and/or one or two or more side ports spaced axially apart along the side wall. Alternatively, the advance segment 22 may be a solid rod which may be slip fit concentrically within the lumen of a cannulated (tubular) needle body 12. Any conductive sections of the needle body 12 or advance segment 22 are preferably provided with a continuous outer polymer jacket to provide electrical insulation of the entire device except where exposure is desired for functioning as an electrode such as the electrode tip 24.

In the illustrated embodiment, proximal end 16 is carried by a hub 26, to which may be attached an electrical connector cable 28 and connector 30. Tubing, adapters or other components may be attached to hub 26 as well, depending upon the desired functionality. A proximal region of the needle body may also have one or more depth markings to indicate distances from distal tip 24, or other important landmarks. Hub 26 may comprise a curve direction or rotational orientation indicator 32 that is located on the same or opposite side of the apparatus 10 as the concave side of the curve 18 in order to indicate the direction of curve 18. Orientation indicator 32 may comprise an ink marking, etching, projection, or other feature that enhance visualization or tactile sensation.

Connector cable 28 may connect to an optional Electrocardiogram (ECG) interface unit via connector 30. An optional ECG connector cable connects an ECG interface unit to an ECG recorder, which displays and captures ECG signals as a function of time. A generator connector cable may connect the ECG interface unit to an energy source such as a generator (not illustrated). In this embodiment, the ECG interface unit can function as a splitter, permitting connection of the electrosurgical tissue piercing apparatus 102 to both an ECG recorder and generator simultaneously. ECG signals can be continuously monitored and recorded and the filtering circuit within the ECG interface unit and may permit energy, for example RF energy, to be delivered from the generator through electrosurgical apparatus 10 without compromising the ECG recorder.

The generator may additionally be configured to detect impedance at the electrode 24 and/or one or more electrodes along the sidewall of the dilator, needle body 12 or advance segment 22, as is discussed in additional detail below.

In another, steerable embodiment (not shown) of apparatus 10, there may be a deflection control on the hub 26 for operating a deflection mechanism associated with the distal zone 18 and/or advance segment 22. One or two or more pull wires may extend from the proximal control to the distal deflection mechanism to actively deflect the distal end in response to manipulation of the control as will be understood in the art. The control mechanism may be used to steer or otherwise laterally deflect at least a portion of distal zone 18 or distal tip.

A generator may be a radiofrequency (RF) electrical generator that is designed to work in a high impedance range. Because of the small size of energy delivery tip 24 the impedance encountered during RF energy application is very high. General electrosurgical generators are typically not designed to deliver energy in these impedance ranges, so only RF generators having certain characteristics can be used with this device.

In one embodiment, the energy is delivered as a continuous wave at a frequency between about 400 kHz and about 550 kHz, such as about 460 kHz, a voltage of between 100 to 200 V RMS and a duration of up to 99 seconds. A grounding pad 130 is coupled to generator 128 for attaching to a patient to provide a return path for the RF energy when generator 128 is operated in a monopolar mode.

Other embodiments could use pulsed or non-continuous RF energy. Some embodiments for pulsed radio frequency energy have radio frequency energy of not more than about 60 watts, a voltage from about 200 Vrms to about 400 Vrms and a duty cycle of about 5% to about 50% at about from slightly more than 0 Hz to about 10 Hz. More specific embodiments include radio frequency energy of not more than about 60 watts, a voltage from about 240 Vrms to about 300 Vrms and a duty cycle of 5% to 40% at 1 Hz, with possibly, the pulsed radio frequency energy being delivered for a maximum of 10 seconds.

In one example, the generator can be set to provide pulsed radio frequency energy of not more than about 50 watts, a voltage of about 270 Vrms, and a duty cycle of about 10% at 1 Hz. Alternatively, the pulsed radio frequency energy could comprise radio frequency energy of not more than about 50 watts, a voltage of about 270 Vrms, and a duty cycle of about 30% at 1 Hz.

In still other embodiments of apparatus 102, different energy sources may be used, such as radiant (e.g. laser), ultrasound, thermal or other frequencies of electrical energy (e.g. microwave), with appropriate energy sources, coupling devices and delivery devices depending upon the desired clinical performance.

Details of exemplary RF needle and generator systems are described below. The RF crossing needle may be a monopolar, conductive canula that is insulated throughout the shaft with only a pre-defined surface area and geometry at the tip exposed for contact on tissue. The electrical circuit is completed through a grounding pad that is electrically connected to the patient's skin. The needle and grounding pad are connected to a battery powered RF generator that delivers a preset, repeatable amount of energy during a discrete time window.

The distal tip of the RF may have a surface area within the range of from about 0.25 mm$^2$ to about 2.5 mm$^2$ Geometry may be annular (e.g., in an implementation having a central aperture), blunt, spherical, typically non-planar.

In addition to the distal tip electrode, a second or third or more electrodes may be provided along the length of the needle or associated dilator. A series of electrodes spaced axially apart may be used such as for depth monitoring and control, as is discussed further in connection with FIGS. 17A-18B, below. The RF generator may include a processor configured to associate a particular electrode in contact with the fossa with a depth of penetration of the needle through the fossa, and display an indicium of that depth. With multiple electrodes, once the tip passes through the fossa, the impedance change is noted. Then as subsequent electrodes are passed through the fossa, each time contact of an electrode with the blood pool or the tissue changes, impedance changes. Each electrode may be in communication with the proximal hub and RF generator by way of a unique electrical conductor, such as a wire or conductive traces embedded between insulator layers in the sidewall.

One or two or five or more side electrodes may be placed within about 0.25 mm to about 20 mm, in some embodiments from about 2 mm to about 10 mm and in one example at least one electrode at about 5 mm from the distal tip, for detecting depth of penetration. At least about two or four or six or ten or more partial or full circumference band electrodes could be spaced uniformly (e.g., every 2-4 mm) along the length of the sidewall proximal to the distal tip. Helical pitch ring electrodes could be utilized if segmented electrodes are utilized. See FIGS. 17A-18B, discussed below.

Preferably the dilator design will accommodate protrusion of the needle tip. Typically, the protrusion will be about 7-8 mm. This allows a series of electrodes on the needle to be used for tissue impedance sensing for depth control.

Electrodes could be 360° annular bands or segmented circumferentially to allow determination of directionality. Independent electrode segments for directionality may include for example two electrodes spaced circumferentially apart and centered on 180° or up to 6 electrodes centered on 60° spacing around the circumference.

One or more electrodes may be used as a reference electrode for blood pool impedance. Bipolar capabilities could be added by the addition of a relatively large surface area grounding electrode. Surface area should be at least about 15× or 20× the area of the ablation electrode, and can be located on a proximal sidewall of the needle, dilator or sheath, anywhere along the length such as from 100 mm proximally of the distal tip or more. The grounding electrode needs exposure to the blood pool, anywhere along the vasculature.

The grounding electrode(s) may alternatively be on the surface of the dilator or sheath, and configured for being in electrical communication with the hub. For example, the needle could have a separate proximal electrode that is in physical, electrical contact with an electrically conductive surface on the ID of the dilator and/or sheath. The sheath and/or dilator are the contact points to the blood pool. Alternatively, the dilator or sheath can be provided with an electrical conductor (wire or conductive polymer) to place the electrode in communication with the hub.

An electrode on the sheath can conveniently act as the bi-polar return electrode as it is continuously in contact with the blood pool. The sheath electrode or any other of the electrodes disclosed herein can also be used to facilitate imaging technologies such as the Kodex EPD imaging and navigation system available from Koninklijke Philips N.V. Such systems measure changing electric field gradients induced on intracardiac electrodes to enable catheter localization and real-time 3D cardiac mapping.

The distal tip of the needle can have specific geometry to aid in performance. The needle can be tapered from the distal tip up to the area where it leaves the dilator: dimensions from 0.050" down to 0.020". Diametral steps may be provided to facilitate tactile feedback to operator as it passes through the septum, such as at about 0.005" increments. The needle preferably has super-elastic characteristics as it extends from the dilator: shape could be simple 'C' or a 90° bend. Needle may exhibit variable flexural rigidity options based on protrusion from dilator to achieve a longer or shorter moment arm. Longer proximal needle shaft with heavier wall tubing, or solid or tubular body.

The distal tip can have features to prevent sliding motion on the fossa, such as surface projections or roughness—shark skin type geometry. Or electrical features such as micropulses of high energy to 'tack' to the tissue.

The proximal end of the shaft may be stiffer than the distal end of the shaft. The wall thickness may vary from about 0.020" down to about 0.005". The dilator may be tapered from a large diameter proximal end down to the standard 0.045" at distal end. The OD may be stepped to create different rigidity characteristics—same effect as tapering, just another way to make the proximal end stiffer.

The flexural rigidity of the shaft may be within the range of from about 0.015 Nm2 to about 0.0008 Nm2, and in some implementations between about 0.010 Nm2 and 0.014 Nm2. The tip and or shaft can be solid or hollow. The shaft can have a constant outside diameter along its length, or can be tapered from larger to smaller in the distal direction, or may be provided with one or two or more stepped diameter transitions 20.

In a cannulated needle implementation the needle can be provided with no ports, a single distal end port, a distal end port plus one or two or three or more side ports, or one or two or three or more side ports with a closed distal end (no end port).

One or more optical sensors may be carried by the distal tip, to visualize location on fossa ovalis and/or evaluate tissue type or condition. Wiring for the optical sensors may be run proximally through a central lumen to an electrical connector carried by the hub 26

The RF generator is preferably self-contained and battery powered, which provides inherent patient safety through the use of independent 12-24 vDC battery power versus connection to an AC power supply. The generator can deliver a high-speed duty cycle from about 0.5 ms to about 10 ms switching for control of output power. Programmable, digital logic for generation of 400-500 kHz RF ablation signal.

The generator is configured for impedance detection for control of power output through control of voltage or duty cycle through high speed programmable logic on an embedded computer processor. The impedance detection is also used for identifying contact with tissue and to confirm penetration of the target tissue wall.

When the RF needle and generator are combined, the system enables automatic tissue detection by impedance change between blood pool contact and tissue contact. When the electrode is within the right atrium or left atrium a first impedance level can be detected. When the electrode comes into contact with the fossa, a second, different impedance can be detected. The second impedance is greater than the first impedance. For example, the first impedance may be within the range of from about 100-200Ω, while the second impedance may be in the range of from about 500-1000Ω. The second impedance may be at least about 50% or 100% or 200% or more higher than the first impedance. The system may further be configured to differentiate tissue types based on tissue impedance (e.g., scar tissue versus absence of scar tissue)

The system may be configured to automatically change a characteristic such as power level based upon impedance changes. This is relevant since with smaller surface area of the electrode tip, and high impedance crossing can be accomplished with lower power.

The impedance measurement enables an automatic power shutoff feature based upon penetration through septum which produces a measurable impedance change. Audible, visual and/or tactile feedback may be provided at milestone events such as when the electrode tip is placed in contact with tissue, and when the electrode tip 24 has penetrated through the fossa and enters the left atrium.

Multiple electrodes may be utilized for redundancy and additional features. A secondary electrode may be spaced proximally apart from the distal tip and positioned in the in the right atrium or left atrium blood pool for reference. A secondary electrode may be used for depth of penetration detection, and/or larger diameter enlargement. A secondary large surface area electrode (e.g., greater than about 15× or 20× the burn electrode surface area) in the proximal shaft may be utilized for bipolar system. Alternatively, the access sheath or dilator may be used as the return electrode.

Additional specifications of an exemplary generator useful to enable the septal crossing by the use of an 400 kHz to 500 kHz RF signal may include the following features.

Voltage output from 7.5 V to 400 V at 460 kHz under the control of the embedded controller. The output power can be controlled by either the output voltage or the duty cycle. Both the voltage and duty cycle are controlled by the embedded controller.

The generator is capable of delivering 50 watts from 40 ohms to 2000 ohms.

The voltage is variable from 7.5 V to 4000 V in 256 steps.
The duty cycle is variable from off to full on in 256 steps.
The duty cycle period is settable in 4 steps 0.556 ms 4.44 ms 0.071 seconds and 1.13 seconds
The generator has a 4×20 LCD display.
The output values are programed by menus by controls such as push buttons.
The time duration power and impedance are displayed during power delivery.
The ablation signal is created by programable logic.
Power for the generator is provided by a 22.2 volt 1350 mah LIPO battery pack.
The signal is generated crystal controlled digitally and converted to sine wave by a series resonate circuit.
The voltage is stepped up by 12× by a high frequency isolation transformer with 8 kv isolation and the resultant signal is coupled to the output by a second series resonate circuit.

Figure 2A:
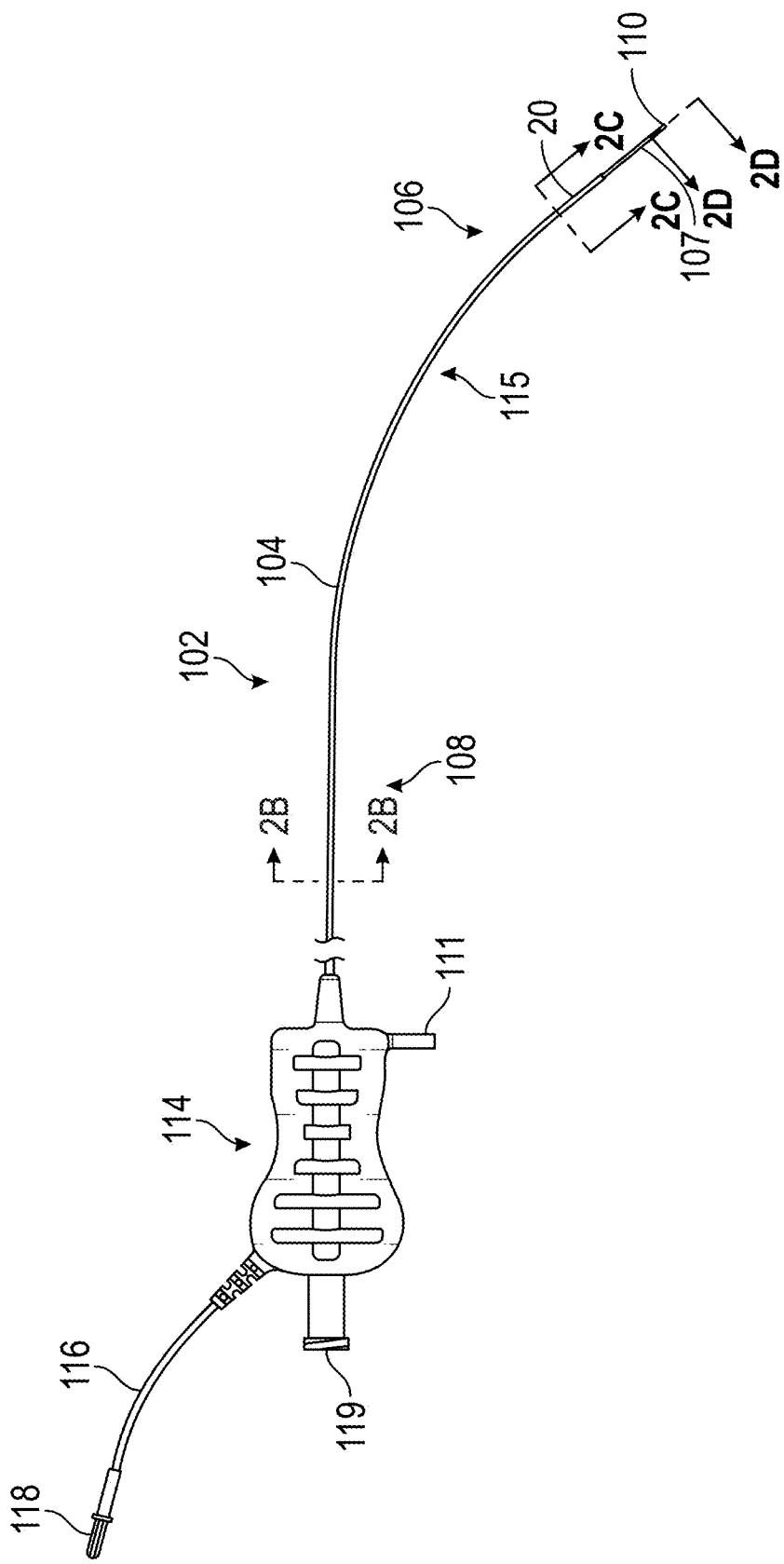
FIG. 2A is a cannulated version of the transseptal crossing needle as in FIG. 1A.

Beginning with FIG. 2A there is illustrated a cannulated embodiment of a tissue penetrating apparatus 102 in a transseptal crossing system of the type having one or more distal ports as will be discussed. Apparatus 102 comprises an elongate tubular body 104 having a distal region 106, and a proximal region 108. Distal region 106 is adapted to be inserted within and along a lumen of a body of a patient, such as a patient's vasculature, and maneuverable therethrough to a desired location proximate material, such as tissue, to be perforated.

Figure 2B:
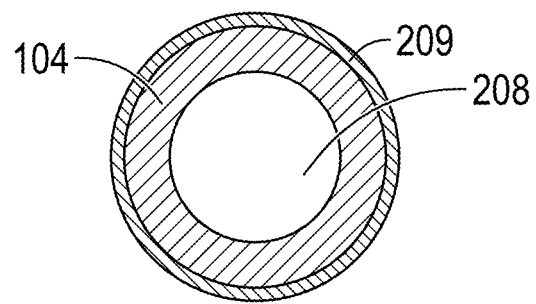
FIG. 2B is a cross section taken along the line A-A in FIG. 2A.
Figure 2C:
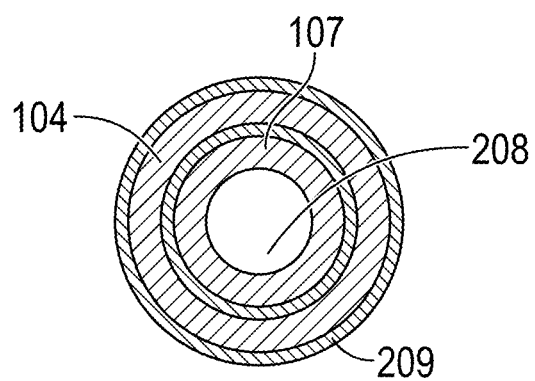
FIG. 2C is a cross section taken along the line B-B in FIG. 2A.
Figure 2D:
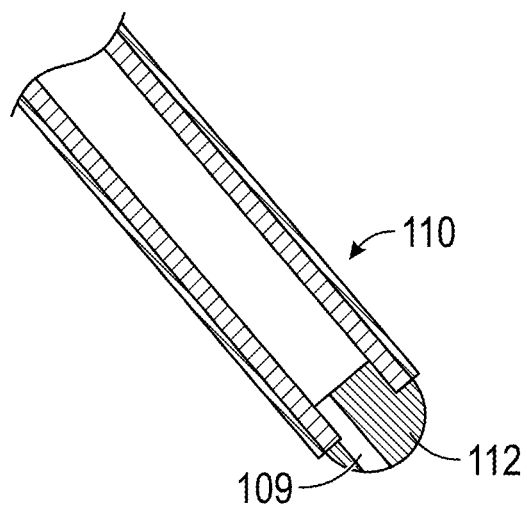
FIG. 2D is a longitudinal cross section taken along the line C-C in FIG. 2A.

The tubular body 104 may have at least one lumen extending from proximal region 108 to distal region 106 such as lumen 208 shown in FIG. 2B. Tubular body 104 may be constructed of a biocompatible polymer material jacket typically with a tubular or solid metal core that provides conductivity and column strength to apparatus 102. Examples of suitable materials for the tubular portion of tubular body 104 are stainless steel or nitinol, with an insulating outer jacket 209 comprising polyetheretherketone (PEEK), nylon, polyimide or other polymers known in the art. In the illustrated embodiment, the outer diameter along the tubular portion of tubular body 104 may step down at transition 20 to distal segment 107. In alternate embodiments, the outer diameter along tubular body 104 remains substantially constant from proximal region 108 to distal segment 107.

Distal region 106 may be provided with a preset curve during manufacturing, typically by exposing it to mechanical force or heat while it is fixed in a desired shape. In an alternate embodiment, the shape of distal region is modifiable by the operator during use. In the present embodiment, the distal region 106 comprises a curve portion 115.

Distal segment 107 may have a smaller outer diameter compared to the remainder of tubular body 104 so that dilation of a perforation is limited while the distal segment 107 is advanced through the perforation. Limiting dilation seeks to ensures that the perforation will not cause hemodynamic instability once apparatus 102 is removed. In some embodiments, the outer diameter of distal segment 107 may be no larger than about 0.8 mm to about 1.0 mm. For example, the outer diameter of distal segment 107 may be about 0.9 mm (about 0.035"). Similarly, in some embodiments, the outer diameter of tubular body 104 may be no larger than about 0.040" to about 0.060". For example, the outer diameter of tubular body 104 may be about 0.050" (1.282 mm).

Distal segment 107 terminates at functional tip region 110, which comprises an energy delivery component and optionally also functions as an impedance and/or ECG measuring device. Functional tip region 110 comprises at least one energy delivery tip 112 made of a conductive and optionally radiopaque material, such as stainless steel, tungsten, platinum, or another metal. Distal region 106 may contain at least one opening 109 which is in fluid communication with main lumen 208 (FIG. 2A) as described further below.

In the illustrated embodiment, proximal region 108 comprises a hub 114, to which are attached a catheter connector cable 116, and electrical connector 118. An adapter 119 such as a Luer connector is attached to hub 114 as well, for placing external fluid sources or devices into communication with the central lumen 208.

Proximal region 108 may also have one or more depth markings 113 to indicate distances from functional tip region 110, or other important landmarks on apparatus 102. Hub 114 comprises a curve direction or orientation indicator 111 that is located on the same side of apparatus 102 as the concave side of the curve 115 in order to indicate the direction of curve 115. Orientation indicator 111 may comprise a projection, etching, or other indicium that facilitates perception of rotational orientation.

Figure 3:
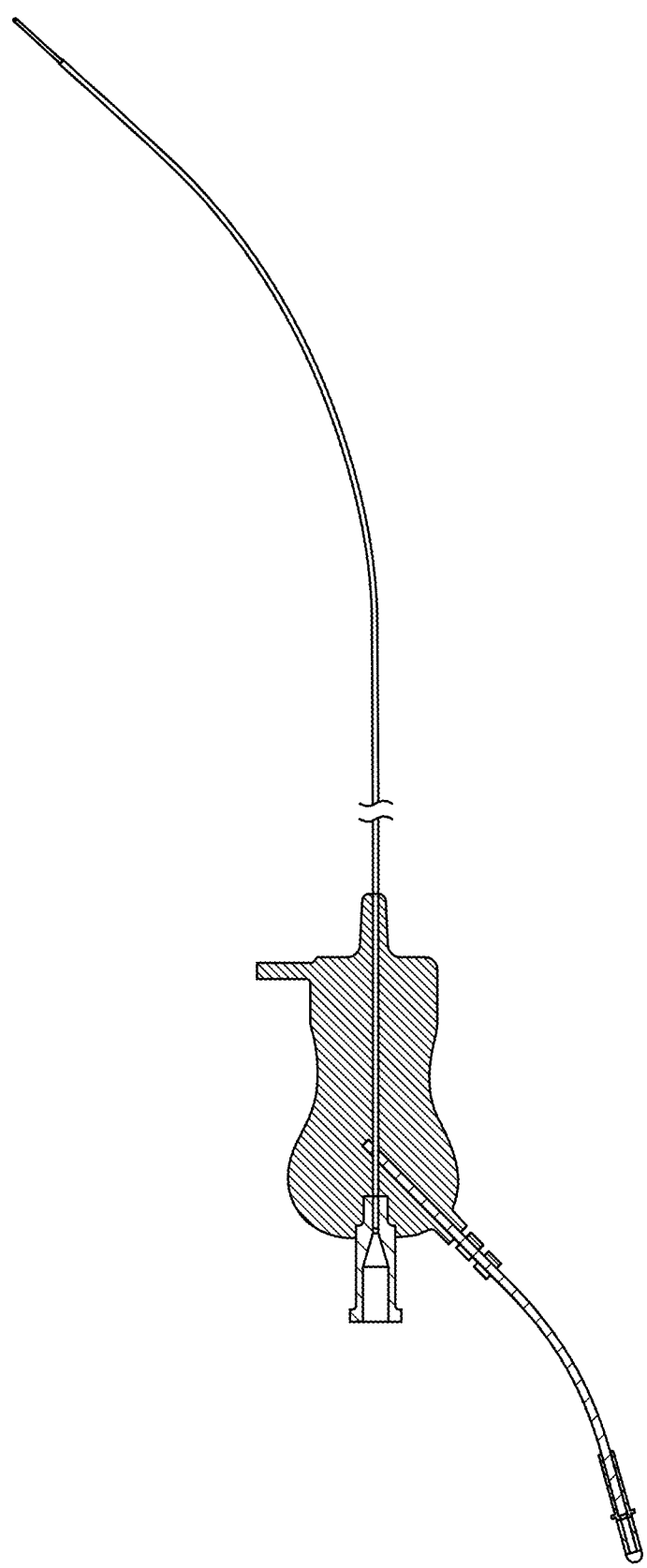
FIG. 3 is a longitudinal cross section through the needle of FIG. 2A.
Figure 4A:
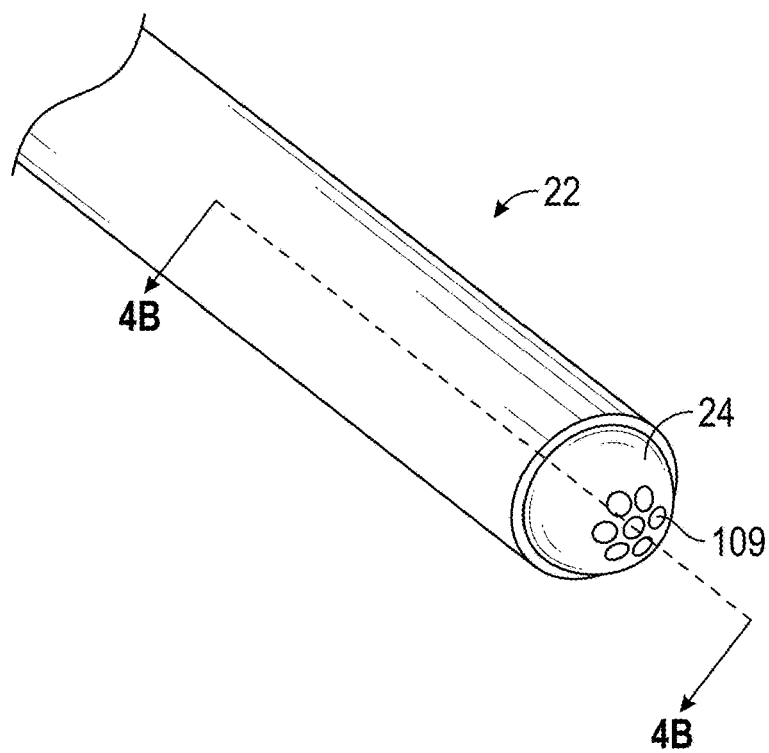
FIG. 4A-4B are detail views of the distal energy delivery tip of one implementation of the invention.
Figure 4B:
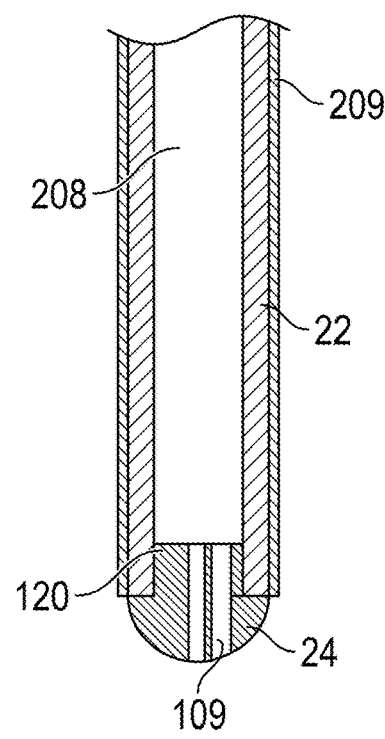

In the illustrated embodiment, adapter 119 is configured to releaseably couple apparatus 102 to an external pressure transducer via external tubing. External pressure transducer is coupled to a monitoring system that converts a pressure signal from external pressure transducer and displays pressure as a function of time. FIG. 3 is a longitudinal cross section through the needle shown in FIG. 2A.

FIGS. 4-10 show different geometries for the distal electrode tip. Referring to FIGS. 4A-4B, the electrode tip 24 may be provided with a plurality such as at least about two or four or six and in the illustrated implementation seven distally facing apertures 109 in communication with the central lumen 208. The electrode tip 24 may be provided with a hemispherical distal surface, and a proximally extending attachment flange 120. Attachment flange 120 may fit within central lumen 208 as illustrated, or may be an annular flange that slip fits over the outside or within an annular recess on the outside surface of the advance segment 22.

Figure 5A:
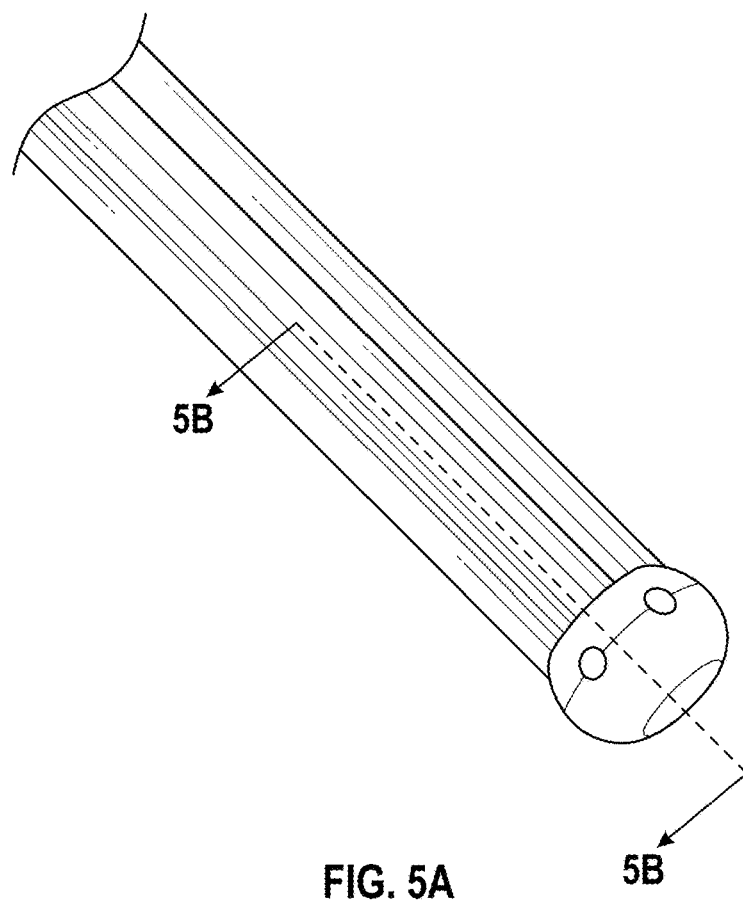
FIG. 5A-5B are detail views of the distal energy delivery tip of another implementation of the invention.
Figure 5B:
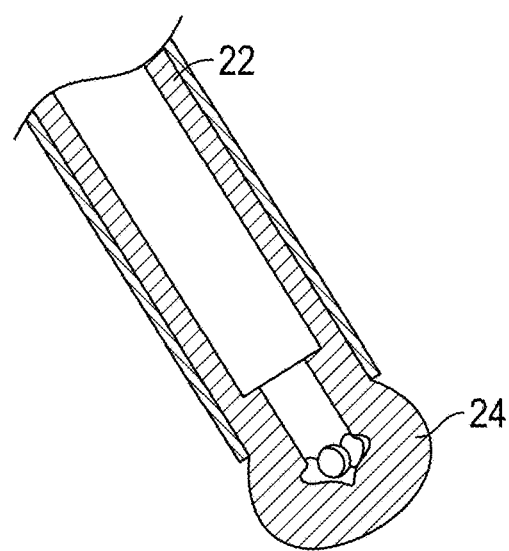

Referring to FIGS. 5A and 5B, the electrode tip 24 may be provided with a diameter is larger than the diameter of the advance segment 22, to increase the electrode footprint. The apertures 109 may be on the distal surface of the tip 24, or may be on a side wall as illustrated in FIG. 5B. The electrode tip 24 may be integrally formed with, or bonded to the advance segment 22.

Figure 6A:
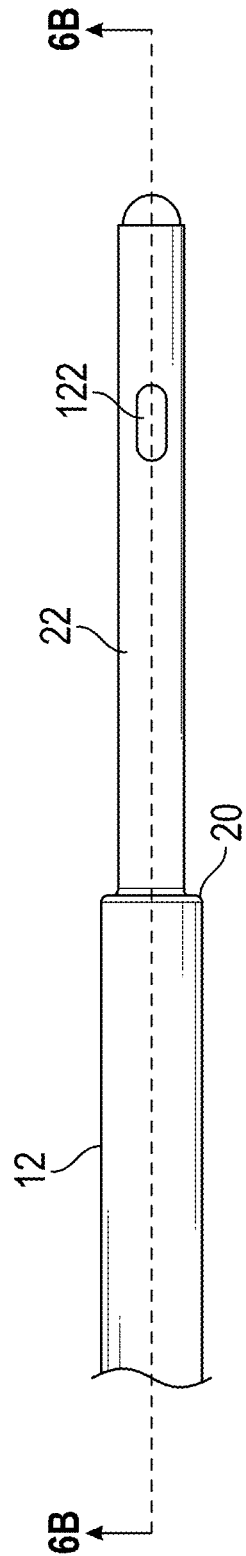
FIG. 6A-6C are detail views of the distal energy delivery tip of another implementation of the invention.
Figure 6B:
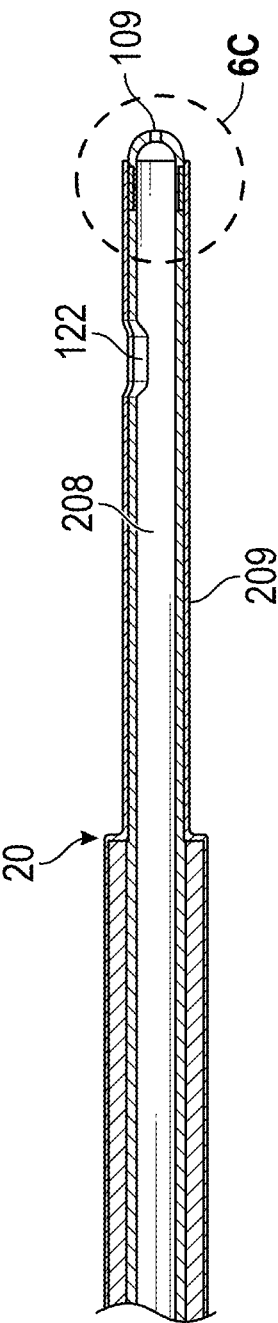
Figure 6C:
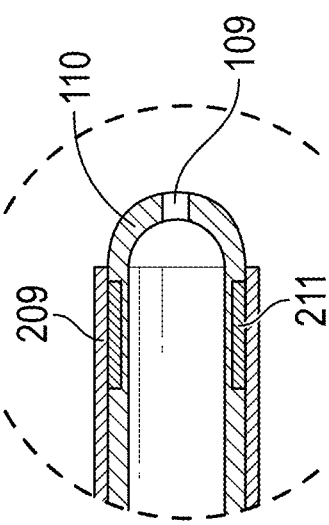

Referring to FIG. 6A-6C, there is illustrated a trans septal crossing needle having both a distal end port 109 and at least one side port 122 on the side wall of a tubular body spaced proximally apart from the distal end port 109. The distal end 110 may be integrally formed with the tubular sidewall 22.

Alternatively, end 110 may be attached to a distal end of the tubular sidewall 22 such as by welding, adhesive, or other technique know in the art. Alternatively, the endcap 110 may be slip fit over the outside of the tubular sidewall 22, such as within an annular recess, to provide a smooth exterior profile. A radiopaque marker 211 such as an annular ring may be embedded within or positioned in an annular recess in the sidewall 22.

Figure 7A:
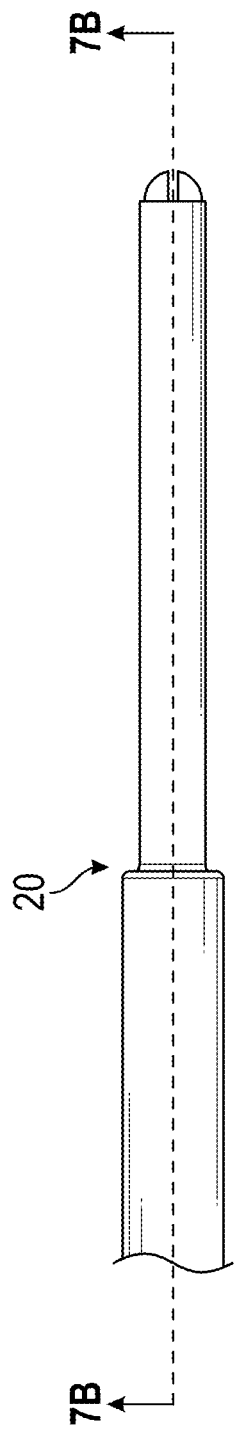
FIG. 7A-7C are detail views of the distal energy delivery tip of another implementation of the invention.
Figure 7B:
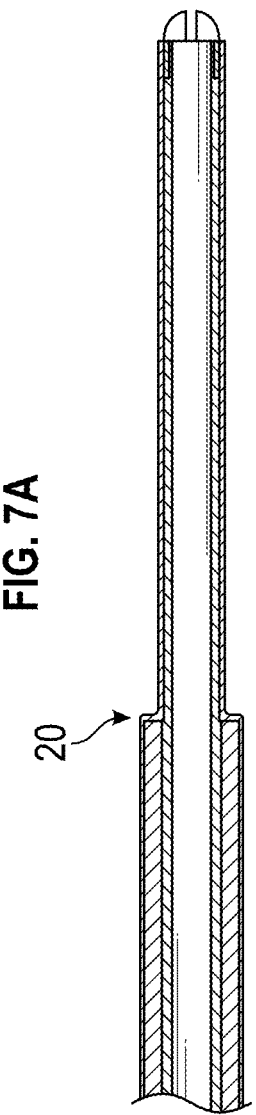
Figure 7C:
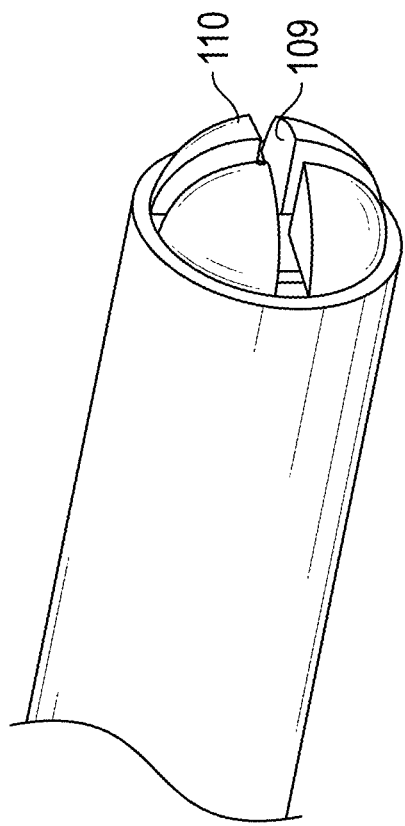

FIG. 7A-7C illustrate an alternative configuration in which the distal end port 109 is in the form of two perpendicular slots In communication with the central lumen 208, and which provide four tissue contacting surfaces for delivering RF energy to the fossa.

Figure 8A:
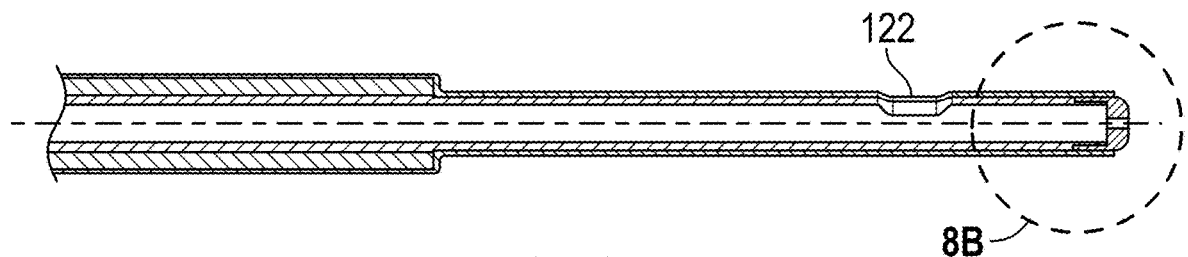
FIG. 8A-8C are detail views of the distal energy delivery tip of another implementation of the invention.
Figure 8B:
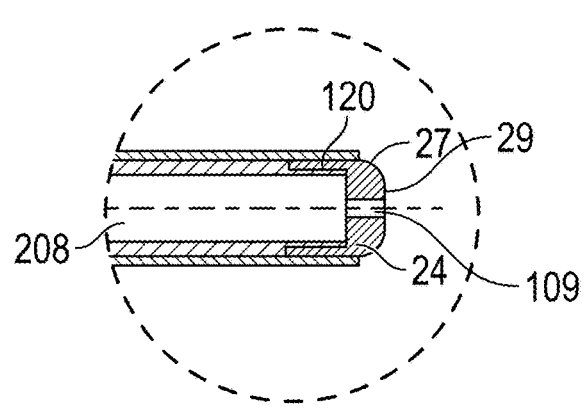

FIGS. 8A and 8B illustrate a distal needle configuration in which the electrode 24 includes an attachment flange 120, such as a proximally extending annular side wall configured to slip fit over the outside of an annular recess in the tubular body 22. A distal aperture 109 is provided in communication with the central lumen 208, as well as an optional one or more side aperture 122. A tubular outer insulating jacket 209 may extend distally over the attachment flange 120, and terminate to expose a distal electrode surface 24. The electrode 24 may include a rounded annular shoulder 27 and a substantially planer transverse distal surface 29 depending upon desired electrical characteristics. Alternatively, the distal surface of the electrode 24 may comprise a hemispherical, constant radius curvature having at least one aperture 109 preferably coaxial with a longitudinal central access of the needle.

Figure 8C:
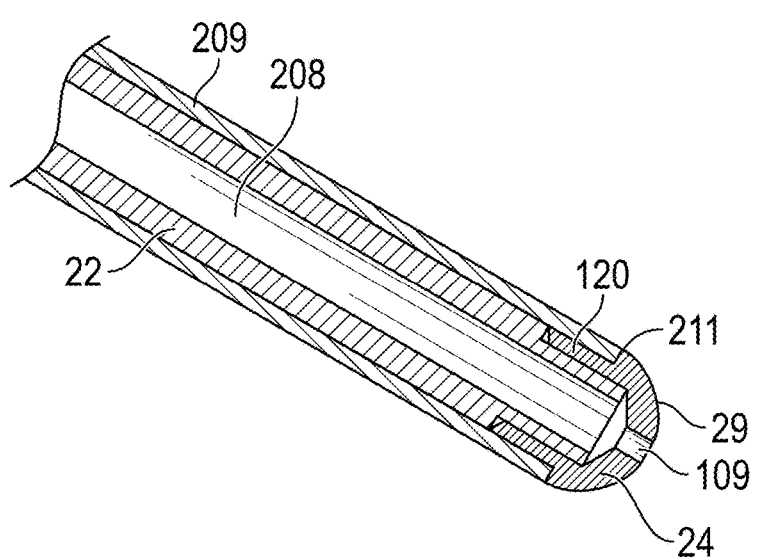

A modified tip configuration is shown in FIG. 8C. A hemispherical distal surface 29 extends proximally to a maximum OD at a step down 211 in outer diameter. The step down 211 is also at the intersection of the hemispherical surface 29 and the proximally extending connector such as an annular attachment flange 120. The OD of the attachment flange 120 is approximately equal to the OD of the needle tubular body 22. With the attachment flange 120 seated within the annular recess on the distal end of the tubular body 22, the adjacent tubular body and the attachment flange 120 provide a uniform OD, over which the insulating jacket 209 resides. Any difference between the OD of the adjacent tubular body 22 and the OD of the attachment flange 120 is generally less than about 0.002' and preferably less than about 0.001". The thickness of the sidewall of insulating jacket 209 is approximately equal to the radial step in OD 211 (e.g., any difference is no more than about 0.001". Thus the overall needle has a smooth constant OD, extending proximally from the electrode tip 24 across the junction between the flange and the tubular body.

In one implementation the electrode tip 24 comprises a radiopaque and highly conductive material, which may be welded to a stainless steel tubular body 22. Preferably the material of the tip will have an electric conductivity of at least about 44 (10.E6 Siemens/m) and a thermal conductivity of at least about 300 W/m.K. In one implementation the electrode tip comprises gold.

The insulating jacket 209 may be a solution coated or electrostatic coated material that is adhesively bonded to the steel tubing. Preferably, the insulating jacket 209 is tough, elastic and conformal.

Selected dimensions of one implementation of the configuration of FIG. 8C appear below. The distal tip 24 and insulating jacket 209 have an OD of no more than about 0.040 inches and in one implementation the OD is about 0.032 inches. The axial length of the tip 24 from the step down 211 to the distal apex is within the range of from about 0.01 to about 0.02 inches and in one implementation is about 0.015 inches. The wall thickness of the attachment flange 120 is generally within the range of from about 0.002 inches to about 0.005 inches and in one implementation is about 0.003 inches. The depth of the annular recess on the proximal side of step down 211 is generally within the range of from about 0.002 inches to about 0.005 inches and in one implementation is about 0.003 inches. The wall thickness of the tubular body at the bottom of the annular recess is generally within the range of from about 0.002 inches to about 0.005 inches and in one implementation is about 0.003 inches. The wall thickness of the insulation layer is generally within the range of from about 0.002 inches to about 0.005 inches and in one implementation is about 0.003 inches. The OD of the annular recess is generally within the range of from about 0.015 inches to about 0.024 inches and in one implementation is about 0.019 inches. The ID of the central lumen is generally within the range of from about 0.008 inches and about 0.016 inches and in one implementation is about 0.013 inches.

Figure 9A:
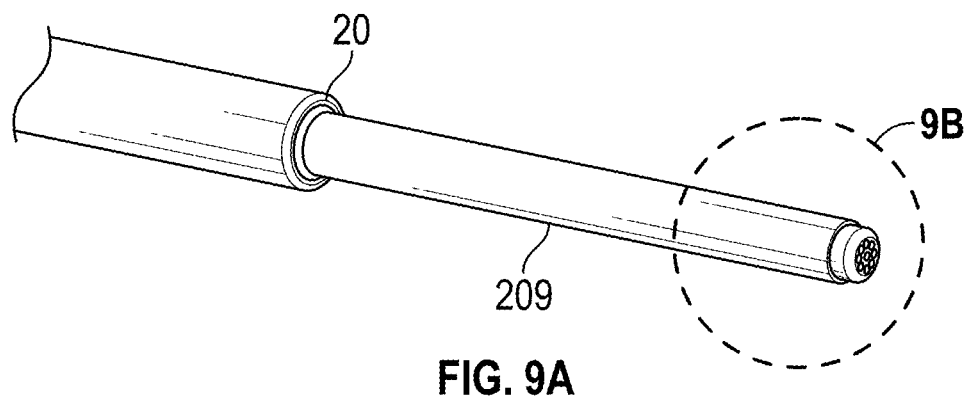
FIG. 9A-9B are detail views of the distal energy delivery tip of another implementation of the invention.
Figure 9B:
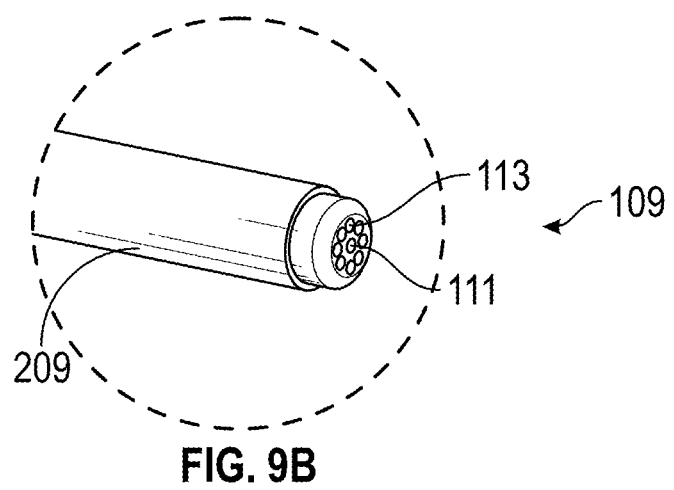

FIGS. 9A-9B illustrate a configuration in which the distal electrode tissue contacting surface is substantially planer, and a plurality of apertures 109 are provided on the distal surface. A central aperture 111 is coaxially aligned with the longitudinal axis of the needle. A plurality of secondary apertures 113 are arranged concentrically about the central aperture 111. At least two or four or six secondary apertures 113 are provided. In the illustrated embodiment, eight aperture surround the central aperture 111. Aperture diameter, number, and density may be determined depending upon the desired clinical performance.

Figure 10A:
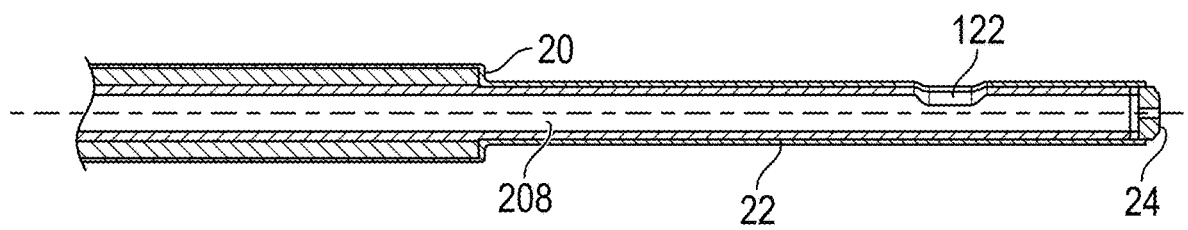
FIG. 10A-10B are detail views of the distal energy delivery tip of another implementation of the invention.
Figure 10B:
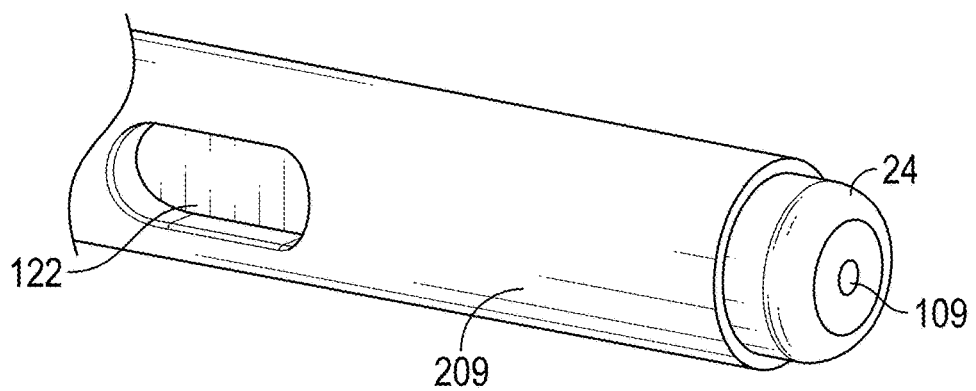

FIGS. 10A-10B illustrate an implementation in which both a distal aperture 109 and at least one side aperture 122 are provided in communication with the central lumen 208. The distal electrode 24 may be integrally formed with the sidewall of the tubular body 22, may be in the form of a cap, slip fit over the distal end of the tubular body, or may be joined at a butt joint to the distal end of the tubular body and secured such as by welding.

Figure 11:
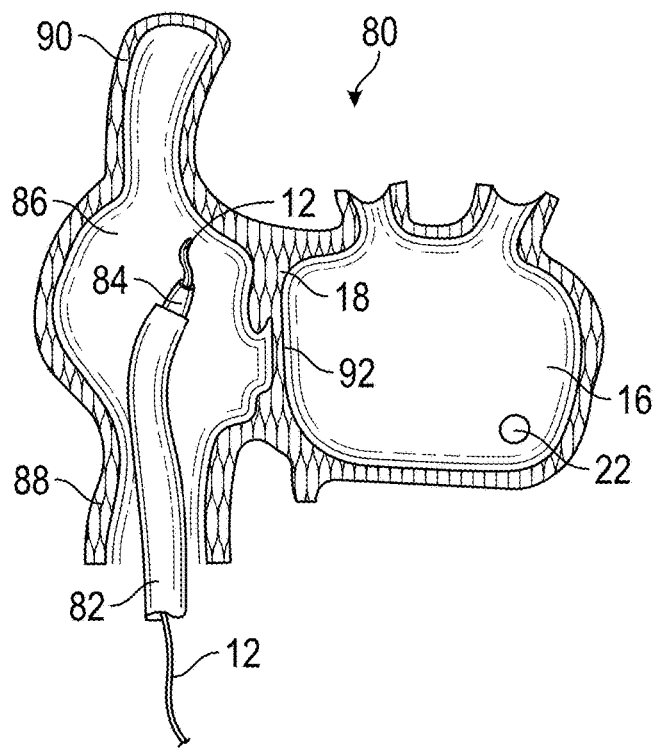
FIG. 11 is a schematic cross section of a portion of a human heart, having a transseptal crossing system of the present invention positioned in the right atrium.

Referring to FIG. 11, there is illustrated a schematic cross-section of a portion of the heart 80. The right atrium 86 is in communication with the inferior vena cava 88 and the superior vena cava 90. The right atrium 86 is separated from the left atrium 16 by the intraatrial septum 18. The fossa ovalis 92 is located on the intraatrial septum 18. As seen in FIG. 11, a large bore transseptal sheath 82 may have a dilator 84, both riding over the RF needle 12 and guidewire, all positioned within the right atrium 86.

Figure 12:
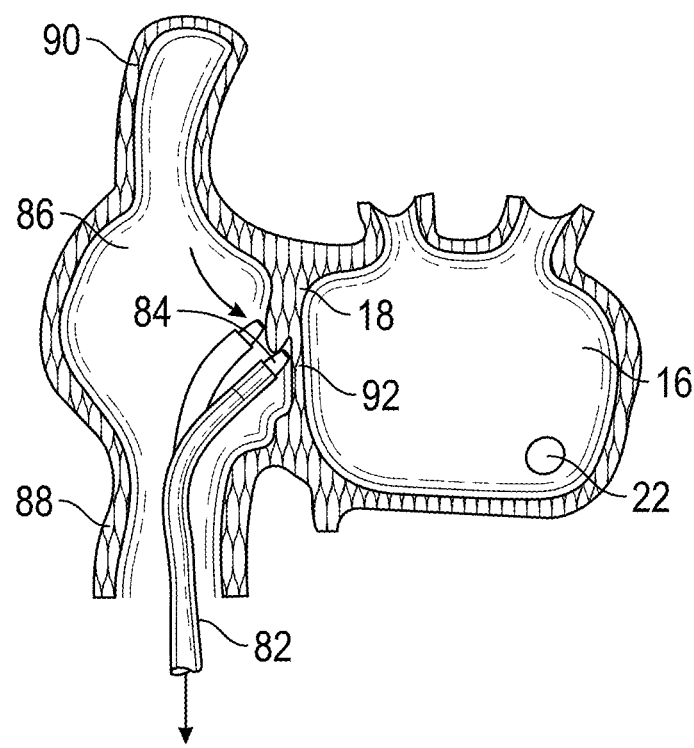
FIG. 12 is a view as in FIG. 11, showing positioning of the distal tip of the transseptal crossing system at the fossa ovalis.

The combination of the sheath 82 with the dilator 84 having the RF needle and GW extending distally therefrom, is then drawn proximally from the superior vena cava while a curved section of the sheath, alone or in combination with a preset curve at the distal region of dilator 84 and or needle 12, causes the tip of the needle 12-GW combination to "drag" along the wall of the right atrium 86 and the septum 18, by proximal traction until the tip pops onto the fossa ovalis 92, as shown in FIG. 12.

After the tip of the needle 12-GW combination has been placed in the desired location against the fossa ovalis 92, RF energy is applied via the tip 24 of the needle 12 to pass through the septum into the LA.

One medical technique is to confirm the presence of the tip of the transseptal needle 12 within the left atrium 16. Confirmation of such location may be accomplished by monitoring the pressure sensed through a transseptal needle lumen to ensure that the measured pressure is within the expected range and has a waveform configuration typical of left atrial pressure. Alternatively, proper position within the left atrium 16 may be confirmed by analysis of oxygen saturation level of the blood drawn through an available lumen; i.e., aspirating fully oxygenated blood. Visualization through fluoroscopy alone, or in combination with the use of dye, may also serve to confirm the presence of the tip of the transseptal 12 and GW in the left atrium 16. As discussed above, a preferred technique for confirming location of the tip is by monitoring a change in impedance at an electrode such as an the side wall of the needle or at the distal tip. 3D mapping by measuring changing electrical field gradients may also be used. The use of multiple electrodes to track tip location is discussed below.

Figure 14A:
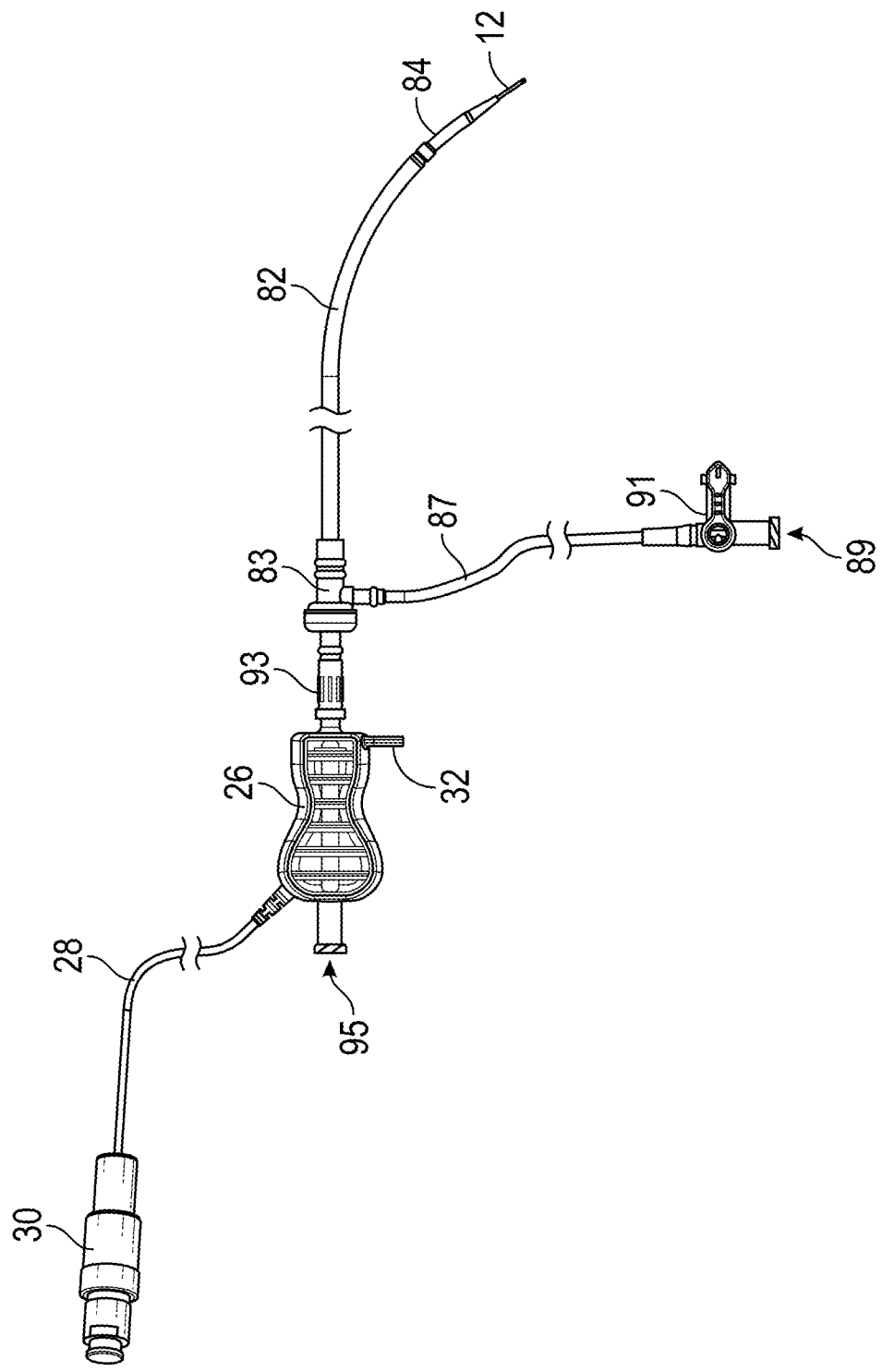
FIG. 14A is a schematic view of an assembled trans septal crossing system, having an RF needle extending through a dilator which is in turn extending through an access sheath.
Figure 14B:
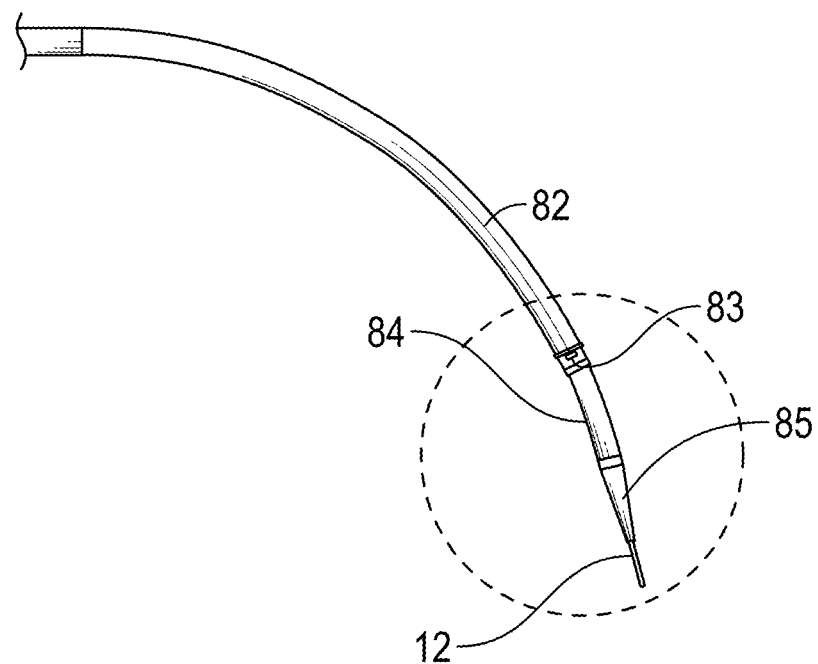
FIG. 14B is an enlarged view of a distal portion of FIG. 14A.
Figure 14C:
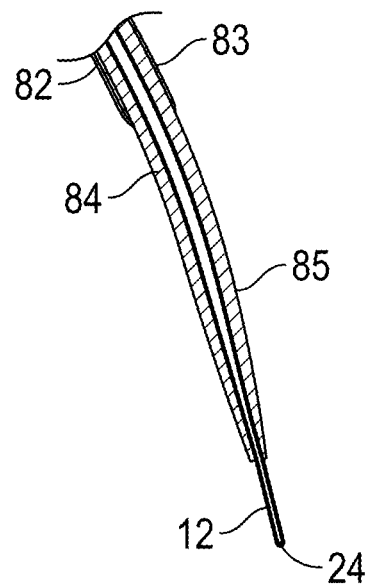
FIG. 14C is a longitudinal cross section through the distal portion shown in FIG. 14B.

FIGS. 14A through 14C illustrate the transseptal crossing system including the RF needle 12 and electrode tip 24 in accordance with the present invention. RF needle 12 is illustrated as extending through a central lumen of dilator 84 and beyond the distal end of the dilator 84. A tapered dilator tip 85 extends between the main body of dilator 84 and a distal aperture. Dilator 84 is illustrated as extending through and beyond the tubular access sheath 82. Access sheath 82 has a plurality of side ports 83 within about 2 cm or 1 cm or less from the distal end of the sheath 82. The inside diameter of the lumen extending through dilator 84 may taper to a smaller ID at the distal tip, at which point a minimal tolerance between the OD of the RF needle 12 and the ID of the dilator 84 is achieved.

A sheath handle 83 is provided at the proximal end of sheath 82 and enables communication of a sheath lumen with a flush line 87 separated from a flush port 89 by stopcock 91. A hemostasis valve (not illustrated) is carried within sheath handle 83.

A dilator handle 93 is provided at the proximal end of the dilator 84. A first interlocking structure on the dilator handle 93 is releasably engageable with a complimentary second interlocking structure on the sheath handle 83 to enable releasable positive engagement between the dilator 84 and the sheath 82. Needle handle 26 is provided with an indicium 32 of directional orientation Of the preset curve as has been discussed. Needle handle 26 is additionally provided with a flush port 95 in fluid communication with the needle 12. Needle handle 26 is additionally provided with a cable 28 leading to an electrical connector 30 for providing electrical communication between the needle 12 and control system which includes the RF power generator. Cable 28 and connector 30 may additionally include electrical conductors in electrical communication with each of any additional electrodes that may be carried by the RF needle 12, dilator 84 or sheath 82.

Figure 15A:
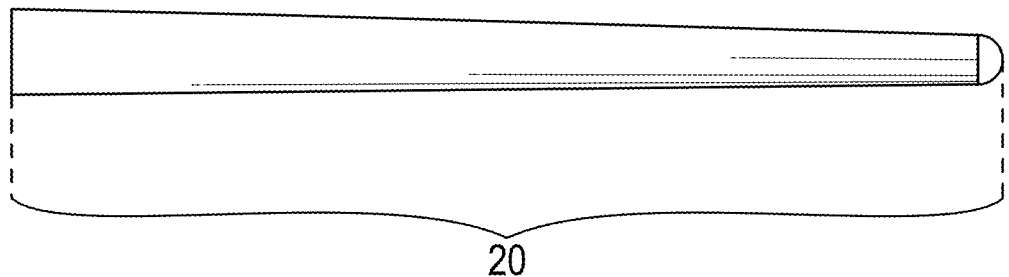
FIG. 15A is a detail view of a tapered portion of the RF needle.
Figure 15B:
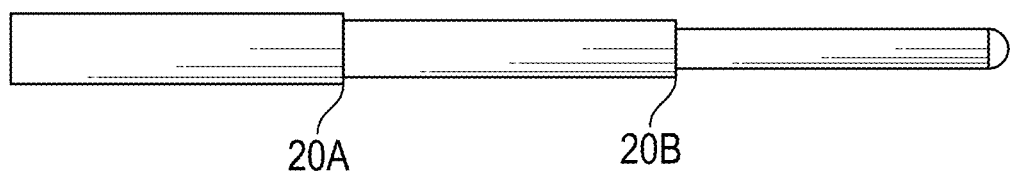
FIG. 15B is a detail view as in FIG. 15A of a stepped outside diameter needle.

As has been described in connection with previous implementations, the RF needle preferably includes at least one transition 20 between a larger diameter proximal section and the distal electrode tip. FIG. 15A schematically illustrates an elongate graduated transition in which the diameter is reduced over a length of at least about 5 millimeters and some implementations at least about 10 mm or 15 mm. In the implementation illustrated in FIG. 15B, a first stepped or tapered transition 20A is provided, spaced apart from an optional second stepped or tapered transition 20B by at least about 2 mm or 4 mm but generally less than about 10 mm. Second transition 20B is generally within the range of from about 8 mm to about 4 mm from the distal tip.

Figure 13:
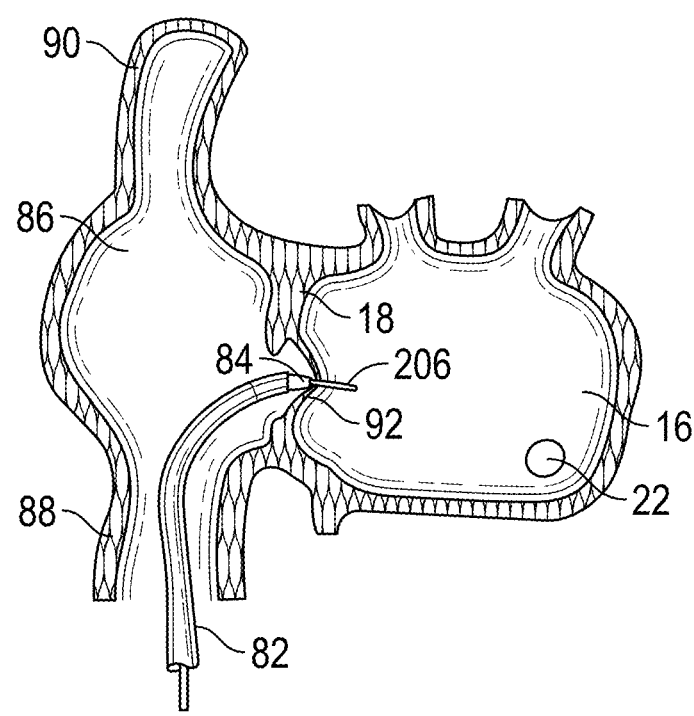
FIG. 13 shows penetration of the guidewire and cannula through the fossa ovalis.

Preferably, at least one of the sheath 82, the dilator 84, and the needle 12 are provided with a preset curve to facilitate crossing the fossa 92. The curve is configured to provide backup support against the wall of the inferior vena cava 88 so that distal advance of the dilator and sheath access assembly will optimize force from the needle against the fossa. Referring to FIG. 13, a greater contact or crossing force would be achieved between the needle and the fossa if the side wall of the sheath 82 were seated against the opposing wall of the inferior vena cava 88. For this purpose, the access assembly may be provided with preset curves such as those illustrated in FIGS. 16A through 16C.

Figure 16A:
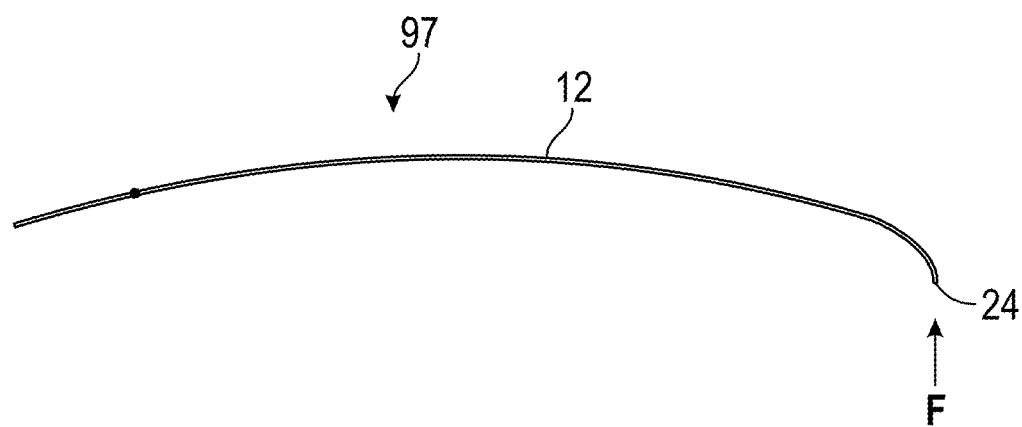
Figure 16B:
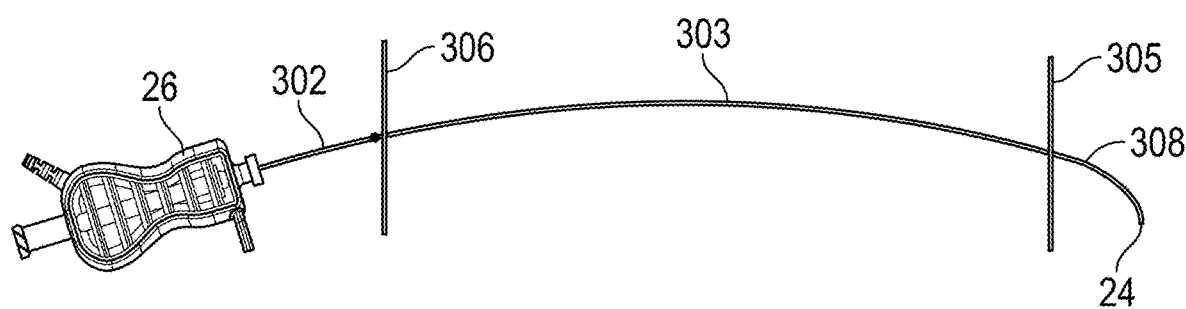

Referring to FIGS. 16A and 16B, there is schematically illustrated a needle 12 having an electrode tip 24. A force vector F illustrates a force vector from the fossa. Preferably, the needle 12 is pre curved with a convex side 97 opposite the electrode tip 24, to help maintain the electrode tip 24 in contact with the fossa.

A proximal handle segment 302 extends between a proximal handle 26 and a transition 306. In one implementation, the handle segment 302 may have an axial length within the range of from about 6 cm to about 14 cm and often within the range of from about 8 cm to about 12 cm. A proximal curved segment 303 may extend distally from the first transition 306 and be preformed with a curve having a best fit radius within the range of from about 75 cm to about 250 cm.

A distal segment 308 extends between a second transition 305 and the distal tip 24. The distal segment 308 may have a length within the range of from about 3 cm to about 10 cm and often within the range of from about 4 cm to about 6 cm. The distal segment 308 is provided with a tighter radius of curvature than proximal segment 303. The best fit radius of curve of the distal segment 308 in the illustrated implementation is generally within the range of from about 5 cm to about 10 cm.

Figure 16C:
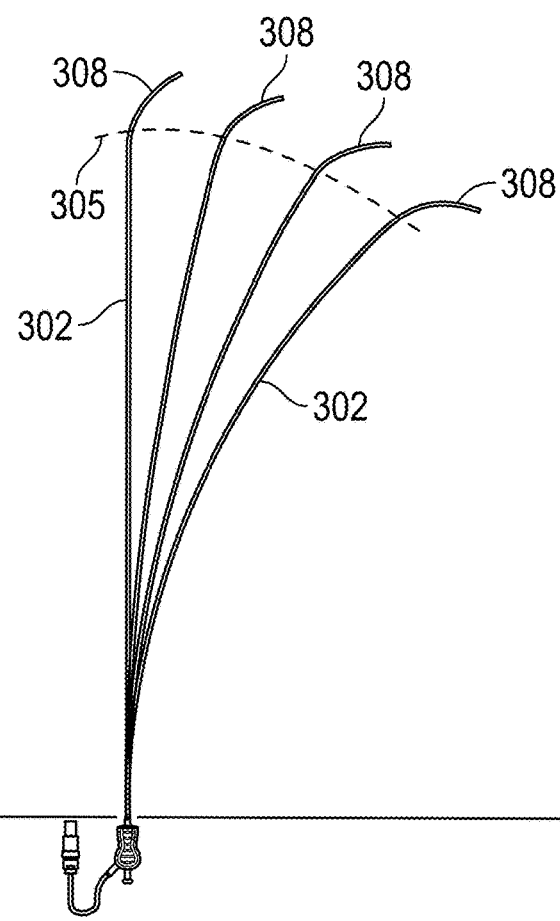

The preformed curvature in four different examples is illustrated in FIGS. 16C and 16D. In each instance, the distal segment 308 has a radius within the range of from about 6 cm to about 9 cm and in one implementation about 8 cm. Proximal segment 302 in one implementation is substantially straight. In a second implementation the proximal segment 302 has a curvature within the range of from about 230 cm to about 250 cm and in one implementation about 240 cm. In another implementation, proximal segment 302 has a curvature within the range of from about 100 cm to about 120 cm and in one implementation about 115 cm. In another implementation proximal segment 302 has a curvature within the range of from about 65 cm to about 85 cm and in one implementation about 76 cm.

FIG. 16D illustrates some specific examples of the needle 12, with dimensions in cm. The distal segment 308 has approximately the same radius in each, labeled 7.6 cm but may be +/−10% or +/−15% from that value depending upon desired clinical performance. The radii ranges for the successive proximal curves 302. Each of the X axis and Y axis dimensions can also be varied by +/−10% or +/−15% from that value depending upon desired clinical performance.

Figure 17A:
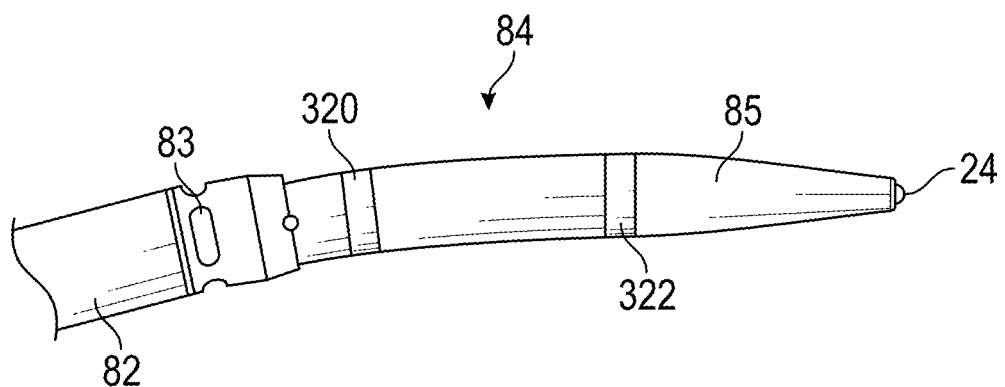
FIGS. 17A-17B show dilators having multiple electrodes.
Figure 17B:
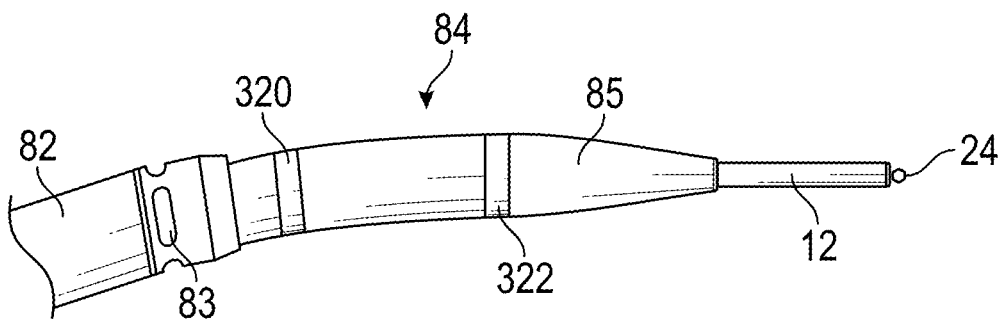

Multi electrode implementations are illustrated in FIGS. 17A through 18B. The crossing assembly is illustrated in FIG. 17A in an imaging configuration. The dilator 84 extends distally of the sheath 82 to expose a first dilator electrode 320 spaced apart from the second dilator electrode 322. A third dilator electrode may be provided on the distal end of taper 85 or on the electrode tip 24 on needle 12. An additional electrode may be carried by the sheath 82, depending upon the desired clinical performance. In a crossing configuration (FIG. 17) the needle 12 extends distally beyond the dilator 84 between about 5 mm and 10 mm.

Figure 18A:
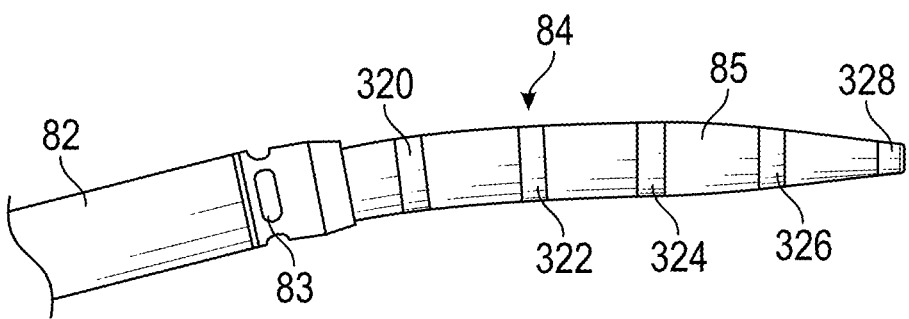
FIGS. 18A-18B show additional multiple electrode dilator configurations.
Figure 18B:
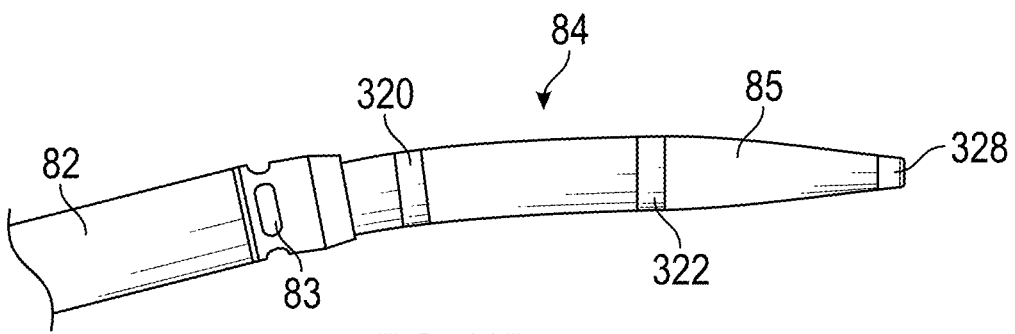

Additional multi electrode implementations are illustrated in FIGS. 18A and 18B. Referring to FIG. 18A, the dilator may additionally be provided with a third dilator electrode 324, and optional 4th dilator electrode 326 and an optional tip dilator electrode 328. The electrodes are preferably evenly spaced apart in an axial direction. Space between electrodes may be at least about 2 millimeters or 4 millimeters or 6 millimeters and generally less than about 12 millimeters or 10 millimeters. The electrodes may have a width in the axial direction within the range of from about 0.5 mm to about 2.5 mm.

Figure 19:
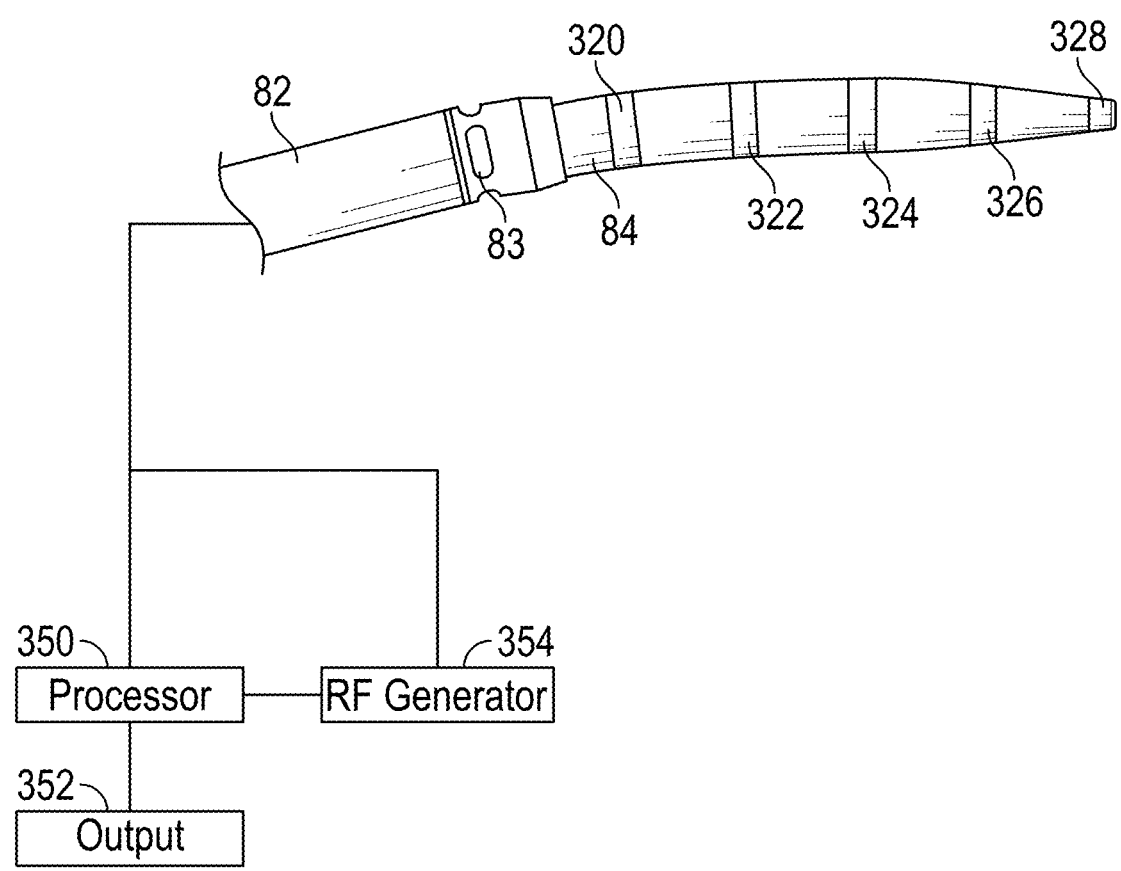
FIG. 19 is a schematic representation of a depth sensing dilator system for dilating a penetration in a tissue plane

Referring to FIG. 19, there is schematically illustrated a representation of a depth sensing dilator system for dilating a penetration in a tissue plane. A tissue plain may be an atrial or ventricular septum, a percutaneous vascular access site, or other tissue plain.

The system includes an elongate flexible body, having a proximal end and a distal end as has been previously discussed herein. A tapered dilator segment is provided on the body. At least a first electrode 328 and a second electrode 326 are spaced axillary apart along the body. The system further includes a processor 350, and an output 352. The processor 350 is configured to send a first signal to the output when the first electrode reaches a predetermined relationship with the tissue plane, and to send a second signal to the output when the second electrode reaches the predetermined relationship with the tissue plane. The predetermined relationship may be when the electrode first contacts the tissue plane, or when the electrode passes through the tissue plane such as into the left atrium blood pool beyond the tissue plane.

The output 352 may comprise at least one of an audio output, a visual output or a tactile output and may be displayed on a graphical user interface on a monitor and or expressed audibly with a constant or pulsed tone or buzzer. At least one electrode is carried on the tapered dilator segment. The first and second electrodes may be spaced axially apart on the tapered dilator segment. The system may further comprise a third and optionally a fourth or fifth or more electrodes spaced proximally of the second electrode. The first second and third and additional electrodes may be approximately equally axially spaced apart as has been previously discussed.

The system further comprises any of the RF generators 354 previously discussed, configured to deliver RF energy to at least one of the first and second electrodes and to conduct impedance measurements. The processor 350 may be configured to determine impedance at at least one of the electrodes. The RF generator may be battery powered as has been previously discussed here in.

What is claimed is:

1. A transseptal crossing system, comprising:
   a transseptal crossing needle comprising:
      an elongate, flexible outer tubular body, having a proximal end, a distal end and an electrically conductive sidewall defining a central lumen;
      an inner tubular body comprising a distal tubular segment extending from the distal end of the outer tubular body;
      an insulation layer surrounding the electrically conductive sidewall of the outer tubular body and a portion of the distal tubular segment and leaving exposed a distal electrode tip, wherein the distal electrode tip is located on the distal tubular segment and defines a distal end of the transseptal crossing needle;
      an end aperture extending distally from the central lumen of the outer tubular body through the distal electrode tip; and
      a hub coupled to the proximal end of the outer tubular body, wherein an axial spacing between the inner tubular body and the hub is fixed; and
   a battery powered RF generator;
   wherein the generator is configured to deliver RF energy to the distal electrode tip and also to measure impedance at the distal electrode tip to provide information about the location of the distal electrode tip, and wherein the generator is configured to detect an impedance change between the distal electrode tip contacting blood pool and the distal electrode tip contacting cardiac tissue.

2. A transseptal crossing system as in claim 1, further comprising at least one side port through the distal tubular segment spaced proximally of the electrode tip.

3. A transseptal crossing system as in claim 1, further comprising at least one side electrode on the distal tubular segment spaced proximally of the electrode tip.

4. A transseptal crossing system as in claim 1, wherein an outside diameter of the distal tubular segment is smaller than an outer diameter of the outer tubular body.

5. A transseptal crossing system as in claim 2, wherein the distal electrode tip comprises a smooth, hemispherical surface.

6. A transseptal crossing system as in claim 1, wherein the sidewall comprises a stainless steel tube.

7. A transseptal crossing system as in claim 1, wherein the tubular body has an outside diameter of about 0.35 inches.

8. A transseptal crossing system as in claim 1, having sufficient structural integrity to guide a large bore catheter transvascularly through a septal wall and into a left atrium of the heart.

9. A transseptal crossing system as in claim 1, which exhibits sufficient structural integrity to guide a large bore catheter transvascularly through a septal wall and into a left atrial appendage of the heart.

10. A transseptal crossing system as in claim 1, comprising an annular recess on a distal end of the distal tubular segment.

11. A transseptal crossing system as in claim 10, wherein the electrode tip includes a proximally extending connector positioned in the recess.

12. A transseptal crossing system as in claim 11, wherein the connector comprises a proximally extending annular flange.

13. A transseptal crossing system as in claim 12, wherein the annular flange has a first outside diameter and an outside diameter of the distal tubular segment on a proximal side of the annular recess is about equal to the first outside diameter.

14. A transseptal crossing system as in claim 13, wherein the electrode tip has a second outside diameter that is greater than the first outside diameter.

15. A transseptal crossing system as in claim 12, wherein the thickness of the insulation layer is about equal to the difference between the first outside diameter and the second outside diameter.

16. A transseptal crossing system as in claim 1, further comprising a dilator having a dilator central lumen for receiving the needle.

17. A transseptal crossing system as in claim 16, further comprising a sheath having a sheath central lumen for receiving the dilator.

18. A transseptal crossing system as in claim 17, further comprising a first electrode on a distal end of the dilator.

19. A transseptal crossing system as in claim 18, further comprising at least a second electrode on the sheath, spaced axially apart from the first electrode.

20. A transseptal crossing system as in claim 19, further comprising a processor configured to determine impedance at least at the first electrode.

* * * * *